US008058410B2

(12) United States Patent
Jungbauer et al.

(10) Patent No.: US 8,058,410 B2
(45) Date of Patent: Nov. 15, 2011

(54) AFFINITY LIGANDS

(75) Inventors: Alois Jungbauer, Vienna (AT); Rainer Hahn, Vienna (AT); Waltraud Kaar, Indooroopilly (AT); Michael Seifert, Vienna (AT); Bernhard Auer, Innsbruck (AT); Clemens Achmüller, Innsbruck (AT); Philipp Wechner, Innsbruck (AT)

(73) Assignees: Sandoz AG, Basel (CH); Boehringer Ingelheim RCV GmbH & Co KG, Vienna (AT)

( * ) Notice: Subject to any disclaimer, the term of this patent is extended or adjusted under 35 U.S.C. 154(b) by 612 days.

(21) Appl. No.: 11/919,258

(22) PCT Filed: Apr. 25, 2006

(86) PCT No.: PCT/AT2006/000167
§ 371 (c)(1),
(2), (4) Date: Oct. 25, 2007

(87) PCT Pub. No.: WO2006/113958
PCT Pub. Date: Nov. 2, 2006

(65) Prior Publication Data
US 2009/0306343 A1 Dec. 10, 2009

(30) Foreign Application Priority Data

Apr. 26, 2005 (GB) .................................. 0508434.8
Apr. 26, 2005 (GB) .................................. 0508435.5
Mar. 16, 2006 (GB) .................................. 0605379.7

(51) Int. Cl.
*A23J 1/00* (2006.01)
*C07K 1/00* (2006.01)
*C07K 14/00* (2006.01)
*C07K 16/00* (2006.01)
*C07K 17/00* (2006.01)
*C07K 5/00* (2006.01)
*C07K 7/00* (2006.01)
*A61K 38/04* (2006.01)

(52) U.S. Cl. ......... 530/413; 530/412; 530/328; 530/329
(58) Field of Classification Search ........................ None
See application file for complete search history.

(56) References Cited

U.S. PATENT DOCUMENTS

2003/0166240 A1 9/2003 Shrader et al.
2005/0036980 A1 2/2005 Chaney et al.
2009/0203069 A1* 8/2009 Jungbauer et al. ........... 435/69.1

FOREIGN PATENT DOCUMENTS

| WO | WO-94/18345 A | 8/1994 |
| WO | WO-98/15572 A | 4/1998 |
| WO | WO-99/14232 A | 3/1999 |
| WO | WO-01/11057 A | 2/2001 |
| WO | WO-02/062969 A2 | 8/2002 |
| WO | WO-02/088171 A2 | 11/2002 |
| WO | WO2009039854 * | 4/2009 |

OTHER PUBLICATIONS

Alloza I et al., "Cross-linking approach to affinity capture of protein complexes from chaotrop-solubilized cell lysates", Analytical Biochemistry, Academic Press, vol. 324, No. 1, Jan. 1, 2004, pp. 137-142.
Database NCBI [Online] 2001, Davoodi-Semiromi A et al.: "Direct submission" XP002397791, retrieved from NCBI, Database accession No. AAL05891, abstract.
Database NCBI [Online] 1999, Hongyuan J & Meiyun Z: "Direct submission" XP002397792, retrieved from NCBI, Database accession No. AAD56386, abstract.
Liu, Ruiwu et al., "Cmbinatorial peptide library methods for immunobiology research", Experimental Hermatology, 2003, vol. 31, pp. 11-30.
Buettner, Joseph A. et al., "Chemically derived peptide libraries: A new resin and methodology for lead identification", Int. J. Peptide Protein Res., 1996, vol. 47, pp. 70- 83.
Alloza I et al., Analytical Biochemistry, Academic Press, vol. 324, No. 1, Jan. 1, 2004, pp. 137-142.
Davoodi-Semiromi A et al., Diabetes, vol. 51, No. 7, 2002, pp. 2334-2336., Isr.

* cited by examiner

*Primary Examiner* — Maury Audet
(74) *Attorney, Agent, or Firm* — Birch, Stewart, Kolasch & Birch, LLP

(57) ABSTRACT

Disclosed is an affinity matrix comprising a solid phase and an affinity ligand comprising peptide bonds coupled to this solid phase, wherein the affinity ligand comprising peptide bond is selected from the following group of ligands: a) peptides comprising the formula $X_1X_2X_3X_4$, wherein $X_1$ to $X_4$ are amino acid residues and at least two of $X_1$ to $X_4$ is W, Y or F; b) peptides comprising the formula $X_5X_6X_7X_8$, wherein $X_5$ to $X_8$ are amino acid residues, at least one of $X_5$ to $X_8$ is W, and at least one of $X_5$ to $X_8$ is E or D; and c) poly-amino acids consisting of an amino acid monomer of the group consisting of R, K, E and D and an amino acid monomer of the group consisting of Y, F and W, preferably poly-KY, poly-KF, poly-KW, poly-RY, poly-RF, poly-RW, poly-EY, poly-DY, poly-EF, poly-EW, poly-DF and poly-DW, with the proviso that the peptides according to a) and b) have a maximum length of 35 amino acid residues and that the poly-amino acids according to c) have a minimum length of 20 amino acid residues.

8 Claims, No Drawings

AFFINITY LIGANDS

The present invention relates to affinity purification techniques and material, especially for affinity chromatography, and specific new ligands for use in such techniques. More specifically, the invention is directed to capturing and purifying $N^{pro}$, $N^{pro}$-mutants, $N^{pro}$ fusion proteins expressed as inclusion bodies under denaturing conditions or proteins with a high aggregation tendency using peptide affinity chromatography.

Affinity chromatography is one of the most efficient techniques for specific isolation of a compound from a crude, complex mixture. Antibodies have been successfully applied as affinity ligands due to their high selectivity and their high affinity. A drawback of these affinity matrices is their relative instability which may lead to leaching of antibody from the support matrix into the product. Furthermore regeneration with alkaline buffers, which is a common procedure in the biopharmaceutical industry, can lead to irreversible denaturing and loss of binding efficiency. Short peptides are capable of replacing antibodies as affinity ligands. These small molecules offer high chemical stability, efficiency, selectivity, low price and they are usually not toxic. These features are considered as an advantage over proteinaceous ligands especially when applied in a biopharmaceutical environment. Peptides directed against a target molecule can be identified from combinatorial peptide libraries or biological libraries. Chemically synthesized combinatorial libraries include pin-synthesis, teabag, SPOT, etc.; biological libraries include phage display techniques, bacterial display, ribosomal techniques, etc.

On the other hand, a lot of proteins show a high tendency to aggregate under physiological conditions or their inherent biological activity is aggregation such as postulated for the prion proteins or amyloid peptides. In order to study these proteins they have to be solubilized under chaotropic conditions, by addition of detergents, in presence of aqueous solutions with extreme pH (acid or basic) and addition of organic solvents such as acetonitrile, ethanol, isopropanol, propanol, pyridine etc. This is often problematic, if not impossible, especially if the proteins should not be harmed in their activity for conducting further research after solubilisation/purification.

Common materials applied in affinity chromatography are usually binding potential binding partners under kosmotrophic or physiological but not under chaotropic conditions. Accordingly, affinity purified components are often eluted from the affinity chromatography material by applying chaotropic conditions.

It is therefore an object of the present invention to provide affinity ligands or affinity material which is able to bind affinity partners under chaotopic conditions. Preferably, this material should be useable in affinity purification of proteins from samples or starting material with chaotopic conditions, especially $N^{pro}$, $N^{pro}$-mutants, $N^{pro}$ fusion proteins expressed as inclusion bodies under denaturing conditions or proteins showing—under physiological conditions—a high tendency to aggregate.

Therefore, the present invention provides an affinity matrix comprising a solid phase and an affinity ligand comprising peptide bonds coupled to this solid phase, wherein the affinity ligand comprising peptide bond is selected from the following group of ligands:
a) peptides comprising the formula $X_1X_2X_3X_4$, wherein $X_1$ to $X_4$ are amino acid residues and at least two of $X_1$ to $X_4$ is W, Y or F;
b) peptides comprising the formula $X_5X_6X_7X_8$, wherein $X_5$ to $X_8$ are amino acid residues, at least one of $X_5$ to $X_8$ is W, and at least one of $X_5$ to $X_8$ is E or D; and
c) poly-amino acids consisting of an amino acid monomer of the group consisting of R, K, E and D and an amino acid monomer of the group consisting of Y, F and W, preferably poly-KY, poly-KF, poly-KW, poly-RY, poly-RF, poly-RW, poly-EY, poly-DY, poly-EF, poly-EW, poly-DF and poly-DW,
with the proviso that the peptides according to a) and b) have a maximum length of 35 amino acid residues and that the poly-amino acids according to c) have a minimum length of 20 amino acid residues.

Preferably, the peptides according to a) and b) (herein also referred to as "oliogopeptides") have a length of 5 to 12, especially of 6 to 8, amino acid residues. Preferably, at least one positively charged amino acid is present in these oligopeptides. The poly-amino acids according to c) have a preferred length of at least 35 amino acid residues, more preferred at least 50 amino acid residues, especially at least 100 amino acid residues. Specifically preferred poly-amino acids are e.g. commercially avaliable poly-amino acids for culture media, such as poly-KW, 4:1 (MW 20.000-50.000 Da; SIGMA product No. P9285), poly-KY, 4:1 (MW 20.000-50.000 Da; SIGMA product No. P4695) or poly-KF, 1:1 (MW 20.000-50.000 Da; SIGMA product No. P3150).

The affinity ligand according to the present invention may be chemically modified, especially acetylated, esterified, amidated, oxidised, reduced or provided with a linker molecule.

The affinity ligand is preferably linked to the solid matrix by covalent bonds. The affinity ligands and matrices according to the present invention have a high affinity to the autoprotease molecules described herein, especially to bind $N^{pro}$, its derivatives and fusion proteins thereof which may be expressed as inclusion bodies. Specifically, these ligands or affinity matrices bind $N^{pro}$, its derivatives and fusion proteins thereof under chaotropic conditions and also under kosmotropic (nonchaotropic, physiological, normal) conditions, at least the $N^{pro}$-part of e.g. a fusion protein. The affinity ligands according to the present invention exert a high degree of specificity for their ability to selectively bind $N^{pro}$, $N^{pro}$ derivatives and fusion polypeptides thereof under denaturing conditions. Within the scope of the present invention such an affinity ligand is directed against the part of the fusion polypeptide according to the invention that exerts autoproteolytic function.

As solid phase material, all materials already applied in the present field are appropriate. Preferably, the solid phase is selected from the group consisting of chromatography material, especially supports based on cellulose, agarose, acrylamide, poly(styrene-divinylbenzene) or ethylene glycol-methacrylate copolymers, microtiter plates, nitrocellulose membranes, microchips, glass plates, or metal coated supports.

According to the present invention various types of solid phase supports may be used, such as the supports based on cellulose, agarose (Sepharose or Macro-Prep gels), dextran (Sephadex gels), acrylamide (Sephacryl, Trisacryl gels), silica (TSK, SW gels), poly(styrene-divinylbenzene) (Source or Poros gels), ethylene glycol-methacrylate copolymers (Toyopearl HW, TSK, PW, fractogel EMD gels) or mixtures, in particular of agarose and dextran (Superdex gel). The supports approved for human or veterinary use by the competent American authorities (FDA for food and drug administration) or the European Union agencies will be more particularly selected. In addition, the support selected must be bonded, preferably by covalent bonding, to the affinity ligand according to the present invention (the support is said to be functionalized). The solid phase matrix may comprise, as the matrix backbone, any natural or synthetic and organic or inorganic material known per se to be applicable in solid phase separation of proteins and other biomolecules, e.g. natural or synthetic polysaccharides such as agar-agar and agaroses; celluloses, cellulose ethers such as hydroxypropyl cellulose, carboxymethyl celluose; starches; gums such as guar gum, and gum arabic, gum ghatti, gum tragacanth, locust bean gum, xanthan gum; pectins; mucins; dextrans; chitins; chitosans; alginates; carrageenans; heparins; gelatins; synthetic polymers such as polyamides such as polyacrylamides and polymethacrylamides; polyimides; polyesters; polyethers; polymeric vinyl compounds such as polyvinylalcohols and polystyrenes; polyalkenes; inorganic materials such as silicious materials such as silicon dioxide including amorphous silica and quartz; silicas; metal silicates, controlled pore glasses and ceramics; metal oxides and sulfides, or combinations of these natural or synthetic and organic or inorganic materials.

The matrix backbone is preferably selected from agar-agar, agaroses, celluloses, cellulose ethers such as hydroxypropyl cellulose, carboxymethyl cellulose, polyamides such as poly(meth)acryl-amides, polyvinylalcohols, silicas, and controlled pore glasses.

Especially interesting solid phase materials as matrix backbones are e.g. agar or agarose beads such as Sepharose and Superose beads from Pharmacia Biotech, Sweden and Biogel A from Biorad, USA; dextran based beads such as Sephadex, Pharmacia Biotech; cellulose based beads and membranes such as Perloza cellulose from Secheza, Czechoslovakia; composite beads such as Sephacryl and Superdex, Pharmacia Biotech; beads of synthetic organic polymers such as Fractogel from Toso-Haas, USA; POROS media from Perceptive Biosystems, USA, Bio-Rex, Bio-Gel P and Macro Prep from Biorad, HEMA and Separon from TESSEK and Hyper D and Trisacryl media from BioSepra, USA, Enzacryl and Azlactone, 3M, USA; beads of siliceous materials such as controlled pore glass, PROSEP, from Bioprocesing, England and Spherocil, BioSepra; and coated silica composites in the form of beads or membranes such as ACTI-DISK, ACTI-MOD and CycloSep from Arbor Technologies, USA.

Typically, the solid phase matrix backbone, as well as the resulting functionalised solid phase matrix, may, e.g., be in the form of irregular particles or spherical beads, membranes or sheets, moulded surfaces, or sticks. The solid phase material may further be fully or partly permeable or completely impermeable to proteins. In a particularly interesting embodiment of the present invention, the matrix is in the form of irregular or spherical beads with sizes in the range of 1-10000 µm, preferably 10-1000 µm; such as 10-60 µm for high performance applications and such as 50-500 µm, preferably 50-300 µm, for preparative purposes.

A particular interesting form of matrix is a density controlled matrix in the form of a conglomerate comprising density controlling particles. These conglomerates are especially applicable in large scale operations for fluidised or expanded bed chromatography as well as different batch-wise chromatography techniques in non-packed columns, e.g. simple batch adsorption in stirred tanks.

The affinity ligands according to the present invention may be attached to the solid phase material by any type of covalent bond known per se to be applicable for this purpose, either by a direct chemical reaction between the affinity ligand according to the present invention and the solid phase material or by a preceding activation of the solid phase material or of the ligand with a suitable reagent known per se making it possible to link the matrix backbone and the ligand. Examples of such suitable activating reagents are epichlorohydrin, epibromohydrin, allyl-glycidylether; bis-epoxides such as butanedioldiglycidylether; halogen-substituted aliphatic compounds such as di-chloro-propanol, divinyl sulfone; carbonyldiimidazole; aldehydes such as glutaric dialdehyde; quinones; cyanogen bromide; periodates such as sodium-meta-periodate; carbodiimides; chlorotriazines such as cyanuric chloride; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides; and hydrazides. Among these, the activating reagents leaving a spacer group SP1 different from a single bond, e.g. epichlorohydrin, epibromohydrin, allylglycidylether; bis-epoxides; halogen-substituted aliphatic compounds; divinyl sulfone; aldehydes; quinones; cyanogen bromide; chloro-triazines; oxazolones; malelmides; pyridyl disulfides; and hydrazides, are preferred.

Especially interesting activating reagents are believed to be epoxy-compounds such as epichlorohydrin, allyl-glycidylether and butanedioldiglycidylether.

For peptide affinity chromatography within the scope of the present invention, any matrix useful for the immobilization of peptide ligands can be used. Preferably Fractogel epoxy (M), from Merck, Darmstadt, Germany) or equally preferred "monolithic chromatography medium" CIM-epoxy is used. The ligands can be immobilized either directly onto the chemically activated backbone of the chromatography matrix, or via a spacer or linker. In the latter case a spacer is coupled to the chromatographic matrix, said spacer is then chemically activated, in order to allow binding of the ligand. Preferably Fractogel epoxy matrices are used in combination with spacers.

In a particularly preferred embodiment of the present invention the spacer is generated by reaction of the chromatographic matrix with diaminodipropylamine (DADPA) and subsequent reaction with succinic anhydride (SA). The resulting terminal carboxy group on the spacer is chemically activated and preferably linked to a terminal amino-group. The ligand is immobilized on the matrix or on the spacer via a reactive group that it comprises. In the case of peptide ligands such reactive groups may be either the amino, carboxy or the sulfhydryl group. Within the present invention anchorage of the peptide on the matrix or the spacer via an amino bond is particularly preferred.

Preferably, the affinity matrix according to the present invention, especially provided as affinity chromatography material, exhibits oligopeptide ligands as defined under a) and b) above or poly-amino acids as defined under c) above.

As used herein the term "oligopeptides" shall refer to proteinaceous compounds, containing at least three amino acids. Usually such oligopeptides have a length of up to 35 amino acids, preferably a length of 4 to 20 amino acid residues.

Accordingly, in a preferred embodiment of the present invention the affinity chromatography system utilizes an oligopeptide ligand of five to twelve amino acids length, more preferred of six to eight amino acids length, especially comprising a tryptophan residue, which ligand selectively binds to the part of the fusion polypeptide exerting autoproteolytic function under chaotropic conditions and maintains binding during change towards as well as under cosmotropic conditions.

This form of affinity chromatography makes use of the specific binding of certain polypeptides to other polypeptides, as for example known from antibodies. Oligopeptides are capable of serving as affinity ligands as well. These molecules offer high chemical stability, efficiency, selectivity, low price and they are usually not toxic. These features are considered as an advantage especially when applied in a biopharmaceutical process. Peptide ligands directed against a target molecule can be identified from combinatorial peptide libraries or biological libraries in a way, known to the person skilled in the art. In the context of the present invention, screening for peptide ligands was performed under chaotropic conditions.

These affinity ligands according to the present invention have turned out to be specifically characterized by their ability to bind $N^{Pro}$ and $N^{Pro}$-fusion proteins (and proteins being or comprising mutants thereof) under denaturing conditions, e.g. 4 M urea.

Methods for peptide synthesis known in the art, are suitable for preparation of the oligopeptide ligands which are subject to the present invention. Preferably though, the peptide ligands are generated by SPOT synthesis, PIN synthesis, teabag synthesis, mix and split method, described in Ruiwu Liu, et al. Experimental Hematology 31 (2003) 11-30 or the PELICAN method, described in Joseph A. Buettner et al., Int. J. Peptide Protein Res. 47 (1996), 70-83. Several linker chemistries can be applied for anchoring of the first amino acid. In one preferred embodiment of the present invention, the ligands are generated separately and afterwards immobilized on the chromatographic matrix. In another preferred embodiment of the present invention, the peptide ligands are synthesized directly on the chromatographic matrix.

The oligopeptide ligand exerts a high degree of specificity. The oligopeptides that are synthesized within the scope of the present invention are characterized by their ability to selectively bind $N^{pro}$, $N^{pro}$ derivatives and fusion polypeptides thereof under denaturing conditions. Within the scope of the present invention such an oligopeptide ligand is directed against the part of the fusion polypeptide according to the invention that exerts autoproteolytic function.

In a further preferred embodiment of the present invention the oligopeptide ligand has an amino acid sequence selected from the group consisting of VSIFEW (SEQ ID NO: 56), AVSIEWY (SEQ ID NO: 115), AVSFIWY (SEQ ID NO: 116), VSFIWYK (SEQ ID NO: 117), ASRFWYA (SEQ ID NO: 102), AFYTWYA (SEQ ID NO: 71), AFYRWYK (SEQ ID NO: 72), AFYRWY (SEQ ID NO: 73), AFYRWYA (SEQ ID NO: 74), AVSIFEWY (SEQ ID NO: 118), AVSRNWY (SEQ ID NO: 119), ASRFWY (SEQ ID NO: 120), AFYRWYAA (SEQ ID NO: 121), AFYRWY (SEQ ID NO: 73), ASRFWYAA (SEQ ID NO: 122), AFYRWYAA (SEQ ID NO: 121) and AFYSWYAA (SEQ ID NO: 123).

Within the scope of the present invention oligopeptide ligands may be used with a free N-terminus or with a blocked N-terminus, blocking being achieved e.g. by ac(et)ylation.

Most preferred is an embodiment of the present invention, wherein the derivative of the naturally occurring Npro of CSFV according to SEQ ID NO 5 (since amino acid sequence of this mutant has a sequence motif "EDDIE" (SEQ ID NO: 124) from residue 53 to 57 (instead of "RGDIR" SEQ ID NO: 183) in the wild type), this mutant (and other mutants comprising this motif) is termed "EDDIE" (SEQ ID NO: 124)-mutant herein) is used in combination with an oligopeptide ligand selected from the group consisting of ASRFWYA (SEQ ID NO: 102), AFYTWYA (SEQ ID NO: 71), AFYRWYK (SEQ ID NO: 72), AFYRWY (SEQ ID NO: 73) and AFYRWYA (SEQ ID NO: 74).

Accordingly, preferred affinity ligands are selected from the group consisting of VSDDWY (SEQ ID NO: 12), VSEDWY (SEQ ID NO: 13), VSIDWY (SEQ ID NO: 14), VSYDWY (SEQ ID NO: 15), VSVDWY (SEQ ID NO: 16), VSWDWY (SEQ ID NO: 17), VSYDWY (SEQ ID NO: 15), VSFDWY (SEQ ID NO: 19), VSDEWY (SEQ ID NO: 20), VSEEWY (SEQ ID NO: 21), VSIEWY (SEQ ID NO: 22), VSYEWY (SEQ ID NO: 23), VSVEWY (SEQ ID NO: 24), VSWEWY (SEQ ID NO: 25), VSYEWY (SEQ ID NO: 23), VSFEWY (SEQ ID NO: 27), DDDDWY (SEQ ID NO: 28), DDEDWY (SEQ ID NO: 29), DDIDWY (SEQ ID NO: 30), DDYDWY (SEQ ID NO: 31), DDVDWY (SEQ ID NO: 32), DDWDWY (SEQ ID NO: 33), DDYDWY (SEQ ID NO: 31), DDFDWY (SEQ ID NO: 35), VSIFWE (SEQ ID NO: 36), FSIFEW (SEQ ID NO: 37), WSIFEW (SEQ ID NO: 38), VSLIWY (SEQ ID NO: 39), VSLIDW (SEQ ID NO: 40), VSLIEW (SEQ ID NO: 41), VSLIWE (SEQ ID NO 42), FSLEEW (SEQ ID NO: 43), VSDLDW (SEQ ID NO: 44), VSDLEW (SEQ ID NO: 45), VSYIDW (SEQ ID NO: VSYIWE (SEQ ID NO: 47)(all these peptides are binding Npro at pH 5.5), VSIDWY, (SEQ ID NO: 14), VSIEWY (SEQ ID NO: 22), VSIWWY (SEQ ID NO: 50), VSIIWY (SEQ ID NO: VSYIWY (SEQ ID NO: 52), VSVIWY (SEQ ID NO: 53), VSFIWY (SEQ ID NO: 54), VSFIWE (SEQ ID NO: 55), VSIFEW (SEQ ID NO: 56), VSIFWE (SEQ ID NO: 36), FSIFEW (SEQ ID NO: 37), WSIFEW (SEQ ID NO: 38), VSLIWY (SEQ ID NO: 39), VSLIDW (SEQ ID NO: 40), VSLIEW (SEQ ID NO: 41), VSLIWE (SEQ ID NO: 42), FSLIEW (SEQ ID NO: 64), WSLIEW (SEQ ID NO: 65), FSYFEW (SEQ ID NO: 66), FSFYEW (SEQ ID NO: 67), WSFYEW (SEQ ID NO: 68), FSYIEW (SEQ ID NO: 69), WSYIEW (SEQ ID NO: 70) (all these peptides are binding Npro at pH 7.3), AFYTWYA (SEQ ID NO: 71), AFYRWYK (SEQ ID NO: 72), AFYRWY (SEQ ID NO: 73), AFYRWYA (SEQ ID NO: 74), AFFRWYA (SEQ ID NO: 75), AFGRWYA (SEQ ID NO: 76), AFHRWYA (SEQ ID NO: 77), AFIRWYA (SEQ ID NO: 78), AFLRWYA (SEQ ID NO: 79), AFMRWYA (SEQ ID NO: 80), AFNRWYA (SEQ ID NO: 81), AFPRWYA (SEQ ID NO: 82), AFQRWYA (SEQ ID NO: 83), AFRRWYA (SEQ ID NO: 84), AFSRWYA (SEQ ID NO: 85), AFTRWYA (SEQ ID NO: 86), AFVRWYA (SEQ ID NO: 87), AFYRWYA (SEQ ID NO: 74), AFYFWYA (SEQ ID NO: 89), AFYGWYA (SEQ ID NO: 90), AFYLWYA (SEQ ID NO: 91), AFYMWYA (SEQ ID NO: 92), AFYNWYA (SEQ ID NO: 93), AFYPWYA (SEQ ID NO: 94), AFYTWYA (SEQ ID NO: 71), AFYVWYA (SEQ ID NO: 96), AFYWWYA (SEQ ID NO: 97), AFYYWYA (SEQ ID NO: 98), AKWFRYA (SEQ ID NO: 99), VSRNWY (SEQ ID NO: 100), ASRNWYA (SEQ ID NO: 101), ASRFWYA (SEQ ID NO: 102), FSRNWYA (SEQ ID NO: 103), VFRNWYA (SEQ ID NO: 104), VWRNWYA (SEQ ID NO: 105), VYRNWYA (SEQ ID NO: 106), VSRAWYA (SEQ ID NO: 107), VSRFWYA (SEQ ID NO: 108), VSRWWYA (SEQ ID NO: 109), VSRYWYA (SEQ ID NO: 110), VSRNFYA (SEQ ID NO: 111), VSRNYYA (SEQ ID NO: 112), VSRNWFA (SEQ ID NO: 113), VSRNWWA (SEQ ID NO: 114) (all these peptides have a specifically high affinity to Npro mutants with the EDDIE (SEQ ID NO: 124) motif in amino acid residues 53 to 57), Ac-AFYTWYAK (SEQ ID NO: 125), Ac-AFYRWYKK (SEQ ID NO: 126), Ac-AFYRWYK (SEQ ID NO: 127), Ac-AFYRWYAK (SEQ ID NO: 128), Ac-AFFRWYAK (SEQ ID NO: 129), Ac-AFGRWYAK (SEQ ID NO: 130), Ac-AFHRWYAK (SEQ ID NO: 131), Ac-AFIRWYAK (SEQ ID NO: 132), AC-AFLRWYAK (SEQ ID NO: 133), AC-AFMRWYAK (SEQ ID NO: 134), AC-AFNRWYAK (SEQ ID NO: 135), AC-AFPRWYAK (SEQ ID NO: 136), AC-AFQRWYAK (SEQ ID NO: 137), AC-AFRRWYAK (SEQ ID NO: 138), AC-AFSRWYAK (SEQ ID NO: 139), AC-AFTRWYAK (SEQ ID NO: 140), AC-AFVRWYAK (SEQ ID NO: 141), AC-AFYRWYAK (SEQ ID NO: 128), AC-AFYFWYAK (SEQ ID NO: 142), AC-AFYGWYAK (SEQ ID NO: 143), AC-AFYLWYAK (SEQ ID NO: 144), AC-AFYMWYAK (SEQ ID NO: 145), AC-AFYNWYAK (SEQ ID NO: 146), AC-AFYPWYAK (SEQ ID NO: 147), AC-AFYTWYAK (SEQ ID NO: 148), AC-AFYVWYAK (SEQ ID NO: 149), AC-AFYWWYAK (SEQ ID NO: 150), AC-AFYYWYAK (SEQ ID NO: 151), AC-AKWFRYAK (SEQ ID NO: 152), AC-VSRNWYK (SEQ ID NO: 153), AC-ASRNWYAK (SEQ ID NO: 154), AC-ASRFWYAK (SEQ ID NO: 155), AC-FSRNWYAK (SEQ ID NO: 156), AC-VFRNWYAK (SEQ ID NO: 157), AC-VWRNWYAK (SEQ ID NO: 158), AC-VYRNWYAK (SEQ ID NO: 159), AC-VSRAWYAK (SEQ ID NO: 160), AC-VSRFWYAK (SEQ ID NO: 161), AC-VSRWWYAK (SEQ ID NO: 162), AC-VSRYWYAK (SEQ ID NO: 163), AC-VSRNFYAK (SEQ ID NO: 164), AC-VSRNYYAK (SEQ ID NO: 165), AC-VSRNWFAK (SEQ ID NO: 166), AC-VSRNWWAK (SEQ ID NO: 167), YWKA (SEQ ID NO: 168), AC-YWKAK (SEQ ID NO: 169), YKYA (SEQ ID NO: 170), AC—YKYAK (SEQ ID NO: 171), YWRA (SEQ ID NO: 172), Ac-YWRAK (SEQ ID NO: 173), ARWY (SEQ ID NO: 174), Ac-ARWYK (SEQ ID NO: 175), YWRA (SEQ ID NO: 172), Ac-YWRAK (SEQ ID NO: 173) (all these peptides have improved immobilisation capabilities to the substrate due to N-terminal acetylation and C-terminal lysination).

It is a specific feature of the affinity matrix according to the present invention that it specifically binds to autoprotease $N^{pro}$ of pestivirus ($N^{pro}$) or $N^{pro}$-mutants, and $N^{pro}$ fusion proteins. The binding of these proteins to the present matrices is so efficient that the proteins are usually also bound under non-chaotropic conditions. Therefore, the matrices according to the present invention are specifically designed with respect to the solid phase and the affinity ligand to allow an efficient binding of autoprotease $N^{pro}$ of pestivirus ($N^{pro}$) or $N^{pro}$-mutants, and $N^{pro}$ fusion proteins both, under chaotropic and non-chaotropic conditions.

According to another aspect, the present invention relates to a method for affinity binding of a protein from a liquid starting preparation, wherein said protein is contacted with an affinity matrix according to the present invention under chaotropic conditions whereby said protein binds to said matrix and separated from said liquid starting preparation.

The terms "kosmotrope" (order-maker) and "chaotrope" (disorder-maker) originally denoted solutes that stabilized, or destabilized respectively, proteins and membranes. Later they referred to the apparently correlating property of increasing, or decreasing respectively, the structuring of water. Such properties may vary dependent on the circumstances, method of determination or the salvation shell(s) investigated. An alternative term used for kosmotrope is "compensatory solute" as they have been found to compensate for the deleterious effects of high salt contents (which destroy the natural hydrogen bonded network of water) in osmotically stressed cells. Both the extent and strength of hydrogen bonding may be changed independently by the solute but either of these may be, and has been, used as measures of order making. It is, however, the effects on the extent of quality hydrogen bonding that is of overriding importance. The ordering effects of kosmotropes may be confused by their diffusional rotation, which creates more extensive disorganized junction zones of greater disorder with the surrounding bulk water than less hydrated chaotropes. Most kosmotropes do not cause a large scale net structuring in water.

Ionic kosmotropes (or: "antichaotropes" to distinguish them from non-ionic kosmotropes) should be treated differently from non-ionic kosmotropes, due mainly to the directed and polarized arrangements of the surrounding water molecules. Generally, ionic behavior parallels the Hofmeister series. Large singly charged ions, with low charge density (e.g. $SCN^-$, $H_2PO_4^-$, $HSO_4^-$, $HCO_3^-$, $I^-$, $Cl^-$, $NO_3^-$, $NH_4^+$, $Cs^+$, $K^+$, $(NH_2)_3C^+$ (guanidinium) and $(CH_3)_4N^+$ (tetramethylammonium) ions; exhibiting weaker interactions with water than water with itself and thus interfering little in the hydrogen bonding of the surrounding water), are chaotropes whereas small or multiply-charged ions, with high charge density, are kosmotropes (e.g. $SO_4^{2-}$, $HPO_4^{2-}$, $Mg^{2+}$, $Ca^{2+}$, $Li^+$, $Na^+$, $H^+$, $OH^-$ and $HPO_4^{2-}$, exhibiting stronger interactions with water molecules than water with itself and therefore capable of breaking water-water hydrogen bonds). The radii of singly charged chaotropic ions are greater than 1.06 Å for cations and greater than 1.78 Å for anions. Thus the hydrogen bonding between water molecules is more broken in the immediate vicinity of ionic kosmotropes than ionic chaotropes. Reinforcing this conclusion, a Raman spectroscopic study of the hydrogen-bonded structure of water around the halide ions $F^-$, $Cl^-$, $Br^-$ and $I^-$ indicates that the total extent of aqueous hydrogen bonding increases with increasing ionic size and an IR study in HDO:$D_2O$ showed slow hydrogen bond reorientation around these halide ions getting slower with respect to increasing size. It is not unreasonable that a solute may strengthen some of the hydrogen bonds surrounding it (structure making; e.g. kosmotropic cations will strengthen the hydrogen bonds donated by the inner shell water molecules) whilst at the same time breaking some other hydrogen bonds (structure breaker; e.g. kosmotropic cations will weaken the hydrogen bonds accepted by the inner shell water molecules). Other factors being equal, water molecules are held more strongly by molecules with a net charge than by molecules with no net charge; as shown by the difference between zwitterionic and cationic amino acids.

Weakly hydrated ions (chaotropes, $K^+$, $Rb^+$, $Cs^+$, $Br^-$, $I^-$, guanidinium$^+$) may be "pushed" onto weakly hydrated surfaces by strong water-water interactions with the transition from strong ionic hydration to weak ionic hydration occurring where the strength of the ion-water hydration approximately equals the strength of water-water interactions in bulk solution (with $Na^+$ being border-line on the strong side and $Cl^-$ being borderline on the weak side). Neutron diffraction studies on two important chaotropes (guanidinium and thiocyanate ions) show their very poor hydration, supporting the suggestion that they preferentially interact with the protein rather than the water. In contract to the kosmotropes, there is little significant difference between the properties of ionic and nonionc chaotropes due to the low charge density of the former.

Optimum stabilization of biological macromolecule by salt requires a mixture of a kosmotropic anion with a chaotropic cation.

Chaotropes break down the hydrogen-bonded network of water, so allowing macromolecules more structural freedom and encouraging protein extension and denaturation. Kosmotropes are stabilizing solutes which increase the order of water (such as polyhydric alcohols, trehalose, trimethylamine N-oxide, glycine betaine, ectoine, proline and various other zwitterions) whereas chaotropes create weaker hydrogen bonding, decreasing the order of water, increasing its surface tension and destabilizing macromolecular structures (such as guanidinium chloride and urea at high concentrations). Recent work has shown that urea weakens both hydrogen bonding and hydrophobic interactions but glucose acts as a kosmotrope, enhancing these properties. Thus, when urea molecules are less than optimally hydrated (about 6-8 moles water per mole urea) urea hydrogen bonds to itself and the protein (significantly involving the peptide links) in the absence of sufficient water, so becoming more hydrophobic and hence more able to interact with further sites on the protein, leading to localized dehydration-led denaturation. Guanidinium is a planar ion that may form weak hydrogen bonds around its edge but may establish strongly-held hydrogen-bonded ion pairs to protein carboxylates, similar to commonly found quaternary structural arginine-carboxylate "salt" links. Also, guanidinium possesses rather hydrophobic surfaces that may interact with similar protein surfaces to enable protein denaturation. Both denaturants may cause protein swelling and destructuring by sliding between hydrophobic sites and consequently dragging in hydrogen-bound water to complete the denaturation.

Generally the kosmotropic/chaotropic nature of a solute is determined from the physical bulk properties of water, often at necessarily high concentration. The change in the degree of structuring may be found, for example, using NMR or vibrational spectroscopy. Protein-stabilizing solutes (kosmotropes) increase the extent of hydrogen bonding (reducing the proton and $^{17}O$ spin-lattice relaxation times) whereas the NMR chemical shift may increase (showing weaker bonding e.g. the zwitterionic kosmotrope, trimethylamine N-oxide) or decrease (showing stronger bonding e.g. the polyhydroxy kosmotrope, trehalose). Trehalose shows both a reduction in chemical shift and relaxation time, as to a lesser extent does the protein stabilizer $(NH_4)_2SO_4$, whereas NaCl only shows a reduction in chemical shift and the protein destabilizer KSCN shows an increase in relaxation time and a reduction in chemical shift. Vibrational spectroscopy may make use of the near-IR wavelength near 5200 $cm^{-1}$ ($v_2+v_3$ combination), which shifts towards longer wavelength (smaller wavenumber) when hydrogen bonds are stronger.

One of the most important kosmotropes is the non-reducing sugar α,α-trehalose. It should perhaps be noted that trehalose has a much more static structure than the reducing sugars, due to its lack of mutarotation, or the other common non-reducing disaccharide, sucrose, due to its lack of a furan ring.

Accordingly, the term "chaotropic conditions" has to be regarded individually on the nature of the liquid starting preparation (which may e.g. be a solution, a suspension, an emulsion, a two- or three phase liquid system, etc.), especially—in preparations containing more than one phase—on the aqueous phase of the preparation. Preferred chaotropic conditions according to the present invention are those which correspond to an urea concentration of 1 to 7 M, especially from 2 to 6 M (preferably in a buffered salt solution, such as 8.0 g NaCl, 0.2 g KCl, 1.44 g $Na_2HPO_4$, 0.24 g $KH_2PO_4$ ad 1000 ml with A. dest., pH 7.4 with HCl). Correspondance of chaotropic conditions (as well as reduction of chaotropicity ("lower" or "less" chaotropic conditions")) may be easily determined by the methods mentioned above as well as by applying the teachings of the Hofmeister series. Addition of various substances in the starting liquid have to be checked in individual cases in order to provide optimum binding/non-aggregating conditions for binding. For example, the use of reduction agents should be optimised to correspond to an amount of 0.05 to 50 mM dithiothreitole (DTT), especially 0.1 to 10 mM DTT. Furthermore, also the addition of detergents may, as described above, influence the chaotropicity of the starting preparation.

Preferably, the protein bound to the matrix is further processed while being bound on said matrix. Such further processing may preferably be a chemical derivatisation, complexation, degradation, etc., especially (in the case of a fusion protein with an autocatalytic moiety) autoproteolysis. This further processing may preferably also be carried out under conditions which are less chaotropic than in the starting material. Usually, optimum conditions for these further processing steps are dependant on the optimum conditions for the processing reaction itself balanced with the needs of keeping the affinity of the protein bound to the affinity matrix to the affinity ligand.

For providing the bound and optionally processed protein in soluble form, the protein has to be eluted again from the carrier or—if provided as a fusion protein comprising an autoproteolytic part and a target protein part—at least the target protein part of the fusion protein. This can be done in many ways. In the case of a fusion protein with an autocatalytic moiety, the elution is performed by the autoproteolytic reaction. In this case, the autoprotease moiety stays at the affinity matrix. In other cases, the protein bound to the matrix or said processed protein is kept at the matrix, preferably even when an elution buffer with a lower chaotropicity as the liquid starting preparation is applied. Preferably, at least the autoproteolytic part of the fusion protein is maintained bound at the matrix.

In other cases, the protein can be kept on the affinity matrix and used as an immobilisate, e.g. for providing immobilised enzymes. Due to the non-covalent, but nevertheless strong, binding of the protein to the solid surface, the immobilised enzyme is usable in industrial processes, especially by providing (enzymatically, catalytically) active surfaces, if the immobilised protein has enzymatic activities.

According to a preferred embodiment of the present invention, the protein is a heterologous recombinant polypeptide which comprises an autoproteolytic moiety and a moiety consisting of a protein of interest which is autoproteolytically cleavable under non-chaotropic conditions by said autoproteolytic moiety, especially fusion proteins wherein the autoproteolytic moiety is autoprotease $N^{pro}$ of pestivirus ($N^{pro}$) or $N^{pro}$-mutants, and $N^{pro}$-fusion proteins expressed as inclusion bodies under denaturing conditions.

According to a preferred embodiment of the a process as described above, the fusion polypeptide comprises a derivative of an autoprotease $N^{pro}$ of CSFV, wherein in addition to the replacement of at least one cysteine residue as described above, at least one basic amino acid residue is replaced by an acidic amino acid residue.

Further preference is given to a derivative of an autoprotease $N^{pro}$ of CSFV, wherein in addition to the replacement of at least one cysteine residue as described above, furthermore, at least one of the following amino acids are exchanged: H5, K16, N35, R53, G54, R57, L143, K145 and R150. A preferred example is a derivative wherein the following amino acids are exchanged: arginine (R) 53 with glutamic acid (E), glycine (G) 54 with aspartic acid (D), arginine (R) 57 with glutamic acid (E), and leucine (L) 143 with glutamine (Q).

Thus in another aspect the present invention relates with further preference to a process as described above, wherein the fusion polypeptide comprises a derivative of an autoprotease $N^{pro}$ of CSFV, wherein in addition to the replacement of at least one cysteine residue as described above, the following amino acids are exchanged: arginine (R) 53 with glutamic acid (E), glycine (G) 54 with aspartic acid (D), arginine (R) 57 with glutamic acid (E), and leucine (L) 143 with glutamine (Q).

In another preferred embodiment of the present invention a derivative of the autoprotease $N^{pro}$ of CSFV comprises the following amino acid sequence:

```
SEQ ID NO 3:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDEAQFEEVTKRIGRVRTGSDGKLYHIYVEVDGEILLKQAK

RGTPRTLKWIRNFTNSPLWVTSC-(168).
```

Thus in another aspect the present invention also relates to a process as described above, wherein the fusion polypeptide comprises a derivative of an autoprotease $N^{pro}$ of CSFV having a sequence according to SEQ ID NO 3.

In yet another aspect the present invention relates to a derivative of the naturally occurring $N^{pro}$ of a Pestivirus, which shows in addition to the reduced aggregation and more neutral pI further enhanced solubility, as compared to the naturally occurring $N^{pro}$ of a Pestivirus.

Solubility is determined as described above.

Accordingly the present invention relates to a derivative of an autoprotease $N^{pro}$ of CSFV, wherein, in addition to the replacement of at least one cysteine residue as described above, at least one hydrophobic amino acid residue is replaced by a hydrophilic residue.

Thus in another aspect the present invention also relates to a process as described above, wherein the fusion polypeptide comprises a derivative of an autoprotease $N^{pro}$ of CSFV, wherein in addition to the replacement of at least one cysteine residue as described above, at least one hydrophobic amino acid residue is replaced by a hydrophilic residue.

Preferred within the present invention is a derivative of an autoprotease $N^{pro}$ of CSFV, wherein in addition to the replacement of at least one cysteine residue as described above furthermore at least one of the following amino acids are replaced: V24, A27, L32, G54, L75, A109, V114, V121, L143, I155 and F158. A preferred example is a derivative wherein the following amino acids are exchanged by threonine (T): alanine (A) 109, valine (V) 114, isoleucine (I) 155 and phenylalanine (F) 158.

Thus in another aspect the present invention relates preferably to a process as described above, wherein the fusion polypeptide comprises a derivative of an autoprotease $N^{pro}$ of CSFV, wherein in addition to the replacement of at least one cysteine residue as described above, the following amino acids are replaced by threonine (T): alanine (A) 109, valine (V) 114, isoleucine (I) 155 and phenylalanine (F) 158. Another, within the present invention more preferred derivative of an autoprotease $N^{pro}$ of CSFV, comprises the following amino acid sequence:

```
SEQ ID NO 4:
(1)-MELNHFELLYKTSKQKPVGVEEPVYDTAGRPLFGNPSEVHPQSTLK

LPHDRGRGDIRTTLRDLPRKGDCRSGNHLGPVSGIYIKPGPVYYQDYTGP

VYHRAPLEFFDETQFEETTKRIGRVTGSDGKLYHIYVEVDGEILLKLAKR

GTPRTLKWTRNTTNCPLWVTSC-(168)
```

Thus in another aspect the present invention more preferably relates to a process as described above, wherein the fusion polypeptide comprises a derivative of an autoprotease $N^{pro}$ of CSFV having a sequence according to SEQ ID NO 4.

Even more preferred within the present invention is a derivative of an autoprotease $N^{pro}$ of CSFV, wherein in addition to the replacement of at least one cysteine residue as described above the following amino acids have been exchanged: alanine (A) 109, valine (V) 114, isoleucine (I) 155 and phenylalanine (F) 158 by threonine (T), arginine (R) 53 with glutamic acid (E), glycine (G) 54 with aspartic acid (D), arginine (R) 57 with glutamic acid (E), and leucine (L) 143 with glutamine (Q).

Thus in another aspect the present invention relates even more preferably to a process as described above, wherein the fusion polypeptide comprises a derivative of an autoprotease $N^{pro}$ of CSFV, wherein in addition to the replacement of at least one cysteine residue as described above the following amino acids have been exchanged: alanine (A) 109, valine (V) 114, isoleucine (I) 155 and phenylalanine (F) 158 by threonine (T); arginine (R) 53 with glutamic acid (E), glycine (G) 54 with aspartic acid (D), arginine (R) 57 with glutamic acid (E), and leucine (L) 143 with glutamine (Q).

Most preferably the derivative of an autoprotease $N^{pro}$ of CSFV according to the present invention comprises the following amino acid sequence:

```
SEQ ID NO 5:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDETQFEETTKRIGRVTGSDGKLYHIYVEVDGEILLKQAKR

GTPRTLKWTRNTTNCPLWVTSC-(168).
```

Thus in another, most preferred aspect the present invention also relates to a process as described above, wherein the fusion polypeptide comprises a derivative of an autoprotease $N^{pro}$ of CSFV having a sequence according to SEQ ID NO 5.

In another equally preferred aspect the present invention relates to a process for the production of heterologous proteins as described above, wherein the fusion polypeptide comprises a derivative of an autoprotease $N^{pro}$ of CSFV having a sequence according to SEQ. ID NO. 5, wherein in addition asparagine (N) 35 is replaced with threonine (T), and threonine (T) 158 is replaced with serine (S).

In another preferred aspect the present invention relates to a process for the production of heterologous proteins as described above, wherein the fusion polypeptide comprises a derivative of an autoprotease $N^{pro}$ of CSFV having a sequence according to SEQ. ID NO. 32, wherein in addition alanine (a) 28 is replaced with glutamic acid (E), serine (S) 71 is replaced with phenylalanine (F) and arginine (R) 150 is replaced with histidine (H).

Preferably in the process according to the present invention the derivative of an autoprotease $N^{pro}$ of CSFV is used in fusion with a protein that contains at least the three first amino acids of proinsulin, more preferably with proinsulin, further more preferably with human proinsulin, most preferably with recombinant human proinsulin, for the production of proinsulin.

It is preferred according to the present invention if the derivative of an autoprotease $N^{pro}$ of CSFV has in addition to the replacement of at least one cysteine residue as described above at least one of the following amino acids exchanged: arginine (R) 53, glycine (G) 54, arginine (R) 57, threonine (T) 109, 114, 155, 158 and leucine (L) 143. Preferred derivatives of the autoprotease $N^{pro}$ of CSFV according to the present invention have in addition to the replacement of at least one cysteine residue as described above, the following amino acids are exchanged: arginine (R) 53 with glutamic acid (E), glycine (G) 54 with aspartic acid (D), arginine (R) 57 with glutamic acid (E), threonine (T) 109, 114, 155, 158 with serine (S) and leucine (L) 143 with glutamine (Q) or asparagine (N) or aspartic acid (D) or serine (S) or histidine.

In other embodiments, especially when the fusion protein should be bound to the affinity matrix according to the present invention also under non-chaotopic condition, the autoproteolytic part of the fusion protein should be inactive or provided in uncleavable form. It is then used only for its affinity properties and not due to its autoproteolytic properties; nevertheless, also those derivatives of NP of CSFV which do—either themselves or due to their linkage to the target molecule part of the fusion protein—not exhibit an autoproteolytic activity when bound to the affinity matrix according to the present invention—even not under non-chaotropic (physiological, "normal") conditions, are also referred to as "autoproteolytic" (moiety).

Preferably, the autoproteolytic moiety is selected from the group consisting of

```
SEQ ID NO 1: (N^pro)
(1)MELNHFELLYKTSKQKPVGVEEPVYDTAGRPLFGNPSEVHPQSTLKL

PHDRGRGDIRTTLRDLPRKGDCRSGNHLGPVSGIYIKPGPVYYQDYTGPV

YHRAPLEFFDEAQFCEVTKRIGRVTGSDGKLYHIYVCVDGCILLKLAKRG

TPRTLKWIRNFTNCPLWVTSC-(168),

SEQ ID NO: 2:
(1)MELNHFELLYKTSKQKPVGVEEPVYDTAGRPLFGNPSEVHPQSTLKL

PHDRGRGDIRTTLRDLPRKGDCRSGNHLGPVSGIYIKPGPVYYQDYTGPV

YHRAPLEFFDEAQFEEVTKRIGRVTGSDGKLYHIYVEVDGEILLKLAKRG

TPRTLKWIRNFTNCPLWVTSC-(168),

SEQ ID NO 3:
(1)MELNHFELLYKTSKQKPVGVEEPVYDTAGRPLFGNPSEVHPQSTLKL

PHDRGEDDIETTLRDLPRKGDCRSGNHLGPVSGIYIKPGPVYYQDYTGPV

YHRAPLEFFDEAQFEEVTKRIGRVTGSDGKLYHIYVEVDGEILLKQAKRG

TPRTLKWIRNFTNCPLWVTSC-(168),

SEQ ID NO 4:
(1)MELNHFELLYKTSKQKPVGVEEPVYDTAGRPLFGNPSEVHPQSTLKL

PHDRGRGDIRTTLRDLPRKGDCRSGNHLGPVSGIYIKPGPVYYQDYTGPV

YHRAPLEFFDETQFEETTKRIGRVTGSDGKLYHIYVEVDGEILLKLAKRG

TPRTLKWTRNTTNCPLWVTSC-(168),

SEQ ID NO 5: ("EDDIE"-xuutant)
(1)MELNHFELLYKTSKQKPVGVEEPVYDTAGRPLFGNPSEVHPQSTLKL

PHDRGEDDIETTLRDLPRKGDCRSGNHLGPVSGIYIKPGPVYYQDYTGPV

YHRAPLEFFDETQFEETTKRIGRVTGSDGKLYHIYVEVDGEILLKQAKRG

TPRTLKWTRNTTNCPLWVTSC-(168),

SEQ ID NO 6:
(1)MELNHFELLYKTSKQKPVGVEEPVYDTAGRPLFGTPSEVHPQSTLKL

PHDRGEDDIETTLRDLPRKGDCRSGNHLGPVSGIYIKPGPVYYQDYTGPV

YHRAPLEFFDETQFEETTKRIGRVTGSDGKLYHIYVEVDGEILLKQAKRG

TPRTLKWTRNSTNCPLWVTSC-(168),

SEQ ID NO 7:
(1)MELNHFELLYKTSKQKPVGVEEPVYDTEGRPLFGTPSEVHPQSTLKL

PHDRGEDDIETTLRDLPRKGDCRFGNHLGPVSGIYIKPGPVYYQDYTGPV

YHRAPLEFFDETQFEETTKRIGRVTGSDGKLYHIYVEVDGEILLKQAKRG

TPHTLKWTRNSTNCPLWVTSC-(168),

SEQ ID 8:
(1)MELNHFELLYKTSKQKPVGVEEPVYDTAGRPLFGNPSEVHPQSTLKL

PHDRGEDDIETTLRDLPRKGDCRSGNHLGPVSGIYIKPGPVYYQDYTGPV

YHRAPLEFFDESQFEESTRRIGRVTGSDGKLYHIYVEVDGEILLKSAXRG

TPRTLKWSRNSTNCPLWVTSC-(168)
and

SEQ ID 9:
(1)MELNHFELLYKTSKQKPVGVEEPVYDTAGRPLFGTPSEVHPQSTLKL

PHDRGRGDIRTTLRDLPRKGDCRSGNHLGPVSGIYIKPGPVYYQDYTGPV

YHRAPLEFFDEAQFCEVTKRIGRVTGSDGKLYHIYVCVDGCILLKLAKRG

TPRTLKWIRNSTNCPLWVTSC-(168).
```

A lot of proteins show a high tendency to aggregate under physiological conditions or their inherent biological activity is aggregation such as postulated for the prion proteins or amyloid peptides. In order to study this proteins they have to be solubilized under chaotropic conditions, by addition of detergents, in presence of aqueous solutions with extreme pH (acid or basic) and addition of organic solvents such as acetonitrile, ethanol, isopropanol, propanol, pyridine etc. The amyloid peptides with high tendency to aggregation are involved in a large number of diseases. A summary of the main amyloidoses and the proteins or peptides involved (Conditions affecting the central nervous system are written in italic):

| Clinical syndrome | Fibril component |
|---|---|
| Alzheimer's disease | Aβ peptides (1-40, 1-41, 1-42, 1-43); Tau |
| Spongiform encephalopathies | Prion protein (full-length or fragments) |
| Parkinson's disease | α-synuclein (wild type or mutant) |
| Fronto-temporal dementias | Tau (wild type or mutant) |
| Familial Danish dementia | ADan peptide |

-continued

| Clinical syndrome | Fibril component |
|---|---|
| Familial British dementia | ABri peptide |
| Hereditary cerebral haemorrhage with amyloidoses | Cystatin C (minus a 10-residue fragment); Aβ peptides |
| Amyotrophic lateral sclerosis | Superoxide dismutase (wild type or mutant) |
| Dentatorubro-pallido-Luysian atrophy | Atrophin 1 (polyQ expansion) |
| Huntington disease | Huntingtin (polyQ expansion) |
| Cerebellar ataxias | Ataxins (polyQ expansion) |
| Kennedy disease | Androgen receptor (polyQ expansion) |
| Spino cerebellar ataxia 17 | TATA box-binding protein (polyQ expansion) |
| Primary systemic amyloidosis | Ig light chains (full-length or fragments) |
| Secondary systemic amyloidosis | Serum amyloid A (fragments) |
| Familial Mediterranean fever | Serum amyloid A (fragments) |
| Senile systemic amyloidosis | Transthyretin (wild-type or fragments thereof) |
| Familial amyloidotic polyneuropathy I | Transthyretin (over 45 variants or fragments thereof) |
| Hemodialysis-related amyloidosis | β2-microglobulin |
| Familial amyloid polyneuropathy III | Apolipoprotein A-1 (fragments) |
| Finnish hereditary systemic amyloidosis | Gelsolin (fragments of the mutant protein) |
| Type II diabetes | Pro-islet amyloid polypeptide (fragments) |
| Medullary carcinoma of the thyroid | Procalcitonin (full-length or fragment) |
| Atrial amyloidosis | Atrial natriuretic factor |
| Lysozyme systemic amyloidosis | Lysozyme (full-length, mutant) |
| Insulin-related amyloid | Insulin (full-length) |
| Fibrinogen α-chain amyloidosis | Fibrinogen (α-chain variants and fragments) |

Another class of proteins the membrane proteins are associated with the so-called membrane bilayer. Biological membranes fulfil vital functions as interfaces to the outside world, as interfaces between cells, and as boundaries of intracellular compartments. Thus, biological membranes are related to numerous diseases such as hyperinsulinemia, nephrogenic diabetes insipidus, congestive heart failure, liver cirrhosis, cystic fibrosis, hyper- and hypotension, lung edema, epilepsy, and cataract. About 30% of the sequenced genes code for membrane proteins. However, only 30 unique structures of membrane proteins have been solved to atomic resolution, compared to 3000 unique crystal structures of soluble proteins, because it is difficult to produce threedimensional (3D) crystals suitable for X-ray analyses from detergent-solubilised membrane proteins. Among the 67 membrane protein structures deposited in the protein data base, 52 are of bacterial origin, suggesting that bacterial membrane proteins are more easily produced, purified and crystallized than those from plants or animals. The challenge now is to solve the structure of membrane proteins from higher organisms and to study their function, dynamics and interaction with ligands. Membrane proteins constitute an important drug target for a large variety of diseases. Preferably, these proteins ("target proteins") are bound as fusion proteins to the affinity matrix. If the target proteins should be provided or further used in immobilised form, the autoproteolytic part of the fusion molecule should be provided in inactive or uncleavable form. The autoproteolytic part then only serves as an affinity handle or tag to immobilise the target protein on the affinity matrix also under non-chaotropic conditions.

Prion diseases, such as variant Creutzfeldt-Jakob disease (vCJD) in people and scrapie in sheep, are characterized by the deposition of PrP$^{Sc}$, an abnormal amyloid protein, in the brain. By changing the conformation of PrP$^C$, PrP$^{Sc}$ propagates throughout the brains of infected people and animals, causing neurodegeneration and death. Over the years, many antibodies have been developed for use in basic research and diagnostics that recognize PrP$^C$ alone or both PrP$^C$ and PrP$^{Sc}$. However, PrP$^{Sc}$-specific anti-bodies have been more elusive.

Membrane proteins (Transmembrane proteins (integral proteins)): Beta-barrel membrane proteins occur in the outer membranes of Gram-negative bacteria, mitochondria and chloroplasts. The membrane-spanning sequences of β-barrel membrane proteins are less hydrophobic than those of α-helical membrane proteins, which is probably the main reason why completely different folding and membrane assembly pathways have evolved for these two classes of membrane proteins. Some β-barrel membrane proteins can be spontaneously refolded into lipid bilayer model membranes in vitro. They may also have this ability in vivo although lipid and protein chaperones likely assist with their assembly in appropriate target membranes. Important other membrane proteins are superantigens.

The present method is excellently suited to provide purified (and optionally immobilised) intact proteins which usually have (under physiological conditions) a high tendency to aggregate and can therefore not be purified by standard methods, especially not by affinity purifications techniques. Since the affinity matrices according to the present invention have the ability to bind proteins under chaotropic conditions, the present method may be used to affinity purify such difficult proteins, especially those proteins which are connected to human diseases. Accordingly, in a preferred embodiment of the present invention the protein to be bound to the present affinity matrix is or comprises a protein or protein moiety which has a high tendency to aggregate under physiological conditions, especially a protein selected from the group consisting of Aβ peptides, Tau Prion protein, α-synuclein, Tau, ADan peptide, ABri peptide, Cystatin C, Aβ peptides, Superoxide dismutase, Atrophin 1, Huntingtin, Ataxins, Androgen receptor, TATA box-binding protein, Ig light chains, Serum amyloid A, Transthyretin, Transthyretin, β2-microglobulin, Apolipoprotein A-1, Gelsolin, Pro-islet amyloid polypeptide, Procalcitonin, Atrial natriuretic factor, Lysozyme, Insulin, Fibrinogen, full-length proteins or specific fragments, mutants, variants or polyQ-expansions thereof.

According to a preferred embodiment of the present invention, the present method is used for the preparation of a heterologous polypeptide, which comprises performing binding to the affinity matrix according to the present invention. Preferably, such a process further comprises the purification of said polypeptide.

In a preferred embodiment of the present invention, a method for affinity binding of a heterologous polypeptide of interest is provided, wherein said polypeptide is expressed as fusion polypeptide of the pestiviral autoprotease N$^{pro}$ or of derivatives thereof, and wherein said fusion polypeptide is contacted under chaotropic conditions with a peptide which exerts under such conditions specific binding to the pestiviral autoprotease $N^{pro}$ or derivatives thereof, and wherein said peptide is bound to a solid phase.

The affinity ligands (the affinity matrices) according to the present invention have the property to selectively bind under chaotropic conditions to the autoprotease $N^{pro}$ of pestivirus ($N^{pro}$) or $N^{pro}$-mutants, and $N^{pro}$fusion-polypeptides of the former two, and to maintain this specific binding during change towards as well as under kosmotropic conditions. The characterizing feature of the affinity ligands according to the present invention is their binding specificity to proteins, especially Npro, Npro mutants, fusion polypeptides and highly aggregating proteins, under chaotropic conditions. This feature renders them useful in any kind of experimental setting that requires specific binding of proteins under chaotropic conditions. In addition the specific binding may be maintained during a change towards and under kosmotropic conditions. It follows that peptides as described above can be used in experimental settings that require binding of the denatured target molecule and maintenance of the binding during refolding and renaturisation of the protein. Accordingly the above described peptides can be used for example in capturing and purifying $N^{pro}$ under denaturing conditions, using peptide affinity chromatography, or else for other forms of affinity purification or affinity assays that involve interaction of a ligand and the protein under chaotropic conditions.

For example, a protein with high tendency to aggregation is fused to $N^{pro}$ or an $N^{pro}$-mutant and then the fusion protein is purified or a raw extract is provided from the expression under chaotropic conditions and is incubated with a surface covered (immobilized) with an affinity ligand according to the present invention. Then the chaotropic conditions are subsequently replaced by conditions which are suited for the further reaction process or analyses, e.g.:

A. The chaotropic conditions are replaced by a physiological buffer and then an immunological reaction is performed using an antibody or antibody fragment directed to a certain domain of the protein. This strategy enables immunological reaction of a protein which has a high tendency to aggregate.

B. The chaotropic conditions are replaced and then a specific chemical reaction is performed to modify the protein structure. Examples are specific oxidization of a amino acid side chain, addition of phosphates or sulfates, addition of a natural of synthetic polymer (e.g. PEGlyation), addition of a peptide chain in order to n-branch the protein molecule, addition of dyes to proteins which are not soluble in physiological solutions or buffers.

C. Single molecule reconstitution of a membrane protein, by fusion of the protein to $N^{pro}$ or an $N^{pro}$-mutant. Molecular handle is immobilized with an affinity ligand according to the present invention against the fusion protein and is bound in presence of 4 M urea. Urea is subsequently removed by detergent and lipid bilayer.

When the binding of the fusion polypeptide to the chromatography system has been accomplished, unbound contaminating components can easily be washed off the column. Such contaminating compounds might for example be host cell polypeptides and nucleic acids, which were occluded into or adsorbed on the inclusion bodies, and remain in the polypeptide solution after solubilisation, as well as residual components from an enzymatic cell disruption. After washing only the fusion polypeptide remains bound to the column so that the following steps are conducted in a purified system.

Binding of the fusion polypeptide is established under chaotropic, inactivating conditions. In order to induce refolding, conditions are changed to kosmotropic.

In a preferred embodiment the step of refolding of the fusion polypeptide is performed by the change from chaotropic to kosmotropic conditions via buffer exchange.

Buffers can be alternatively gradually or instantaneously changed to kosmotropic conditions. In one preferred embodiment of the present invention the exchange of chaotropic buffer with kosmotropic buffer is conducted instantaneously, by application of the buffer as a plug. In another equally preferred embodiment of the present invention the exchange of buffers is conducted gradually.

Binding of the fusion polypeptide to the column and/or refolding and cleaving of said fusion polypeptide might be facilitated if the buffer exchange is accompanied by a temperature adjustment. This can, for example, be introduced by a cooling/heating jacket. Therefore, in a preferred embodiment, a cooling/heating jacket is applied for temperature adjustment; more preferably, the buffer is brought to the desired temperature prior to its application. In this way such temperature adjustment is achieved.

Upon change of conditions in the packed bed the fusion polypeptide starts to refold and the part exerting the autoproteolytic function becomes active. As a result, the C-terminally fused polypeptide of interest is cleaved off at a distinct site defined by the specificity of the autoproteolytic part, thereby producing a homogeneous N-terminus of the polypeptide of interest. Depending on the time required for refolding of the fusion polypeptide, the velocity of the mobile phase with the kosmotropic buffer is reduced or stopped when all chaotropic buffer is displaced from the packed bed. After refolding is complete, the liberated polypeptide of interest is washed out from the packed bed by further feeding of kosmotropic buffer. The N-terminal autoproteolytic part of the fusion polypeptide as well as uncleaved fusion polypeptide is eluted by conventional means, e.g. high salt concentration, a pH-change or NaOH, to regenerate the chromatography material. For regeneration the packed bed is washed with a buffer that strips the autoprotease from the adsorbent. These buffers comprise either acidic or alkaline solutions or organic solvents. After re-equilibration with starting buffer/chaotropic buffer the packed bed is ready for the next cycle.

On the other hand, fusion proteins can be provided which upon correct refolding remain autocatalytically inactive, e.g. by a suitable linker between autoproteolytic part and the target protein part of the fusion protein or by an inactivated mutant, e.g. an autoprotease mutant with no or reduced autoproteolytic activity. For example, a tripeptide linker (amino acids 1, 2 and 3) can be provided between the two parts which has on position 1 and preferably also on positions 2 and 3 basic (R, K, H), acidic (D, E), large hydrophobic (V, L, I M) or aromatic amino acids (F, Y, W) for preventing autoproteolytic cleavage. Examples of inactive autoprotease derivatives are Npro R53E, G54D, R57E, T59M, D92N, A109S, C112E, V114S, V121K, C134E, C138E, L143N, I155S, F158S (1)MELNHFELLYKTSKQKPVGVEEPVYD-
TAGRPLFGNPSEVHPQSTLKLPHDRGEDDIE TML-
RDLPRKGDCRSGNHLGPVSGIYIKPG-
PVYYQNYTGPVYHRAPLEFFDESQFEESTK
RIGRVTGSDGKLY-
HIYVEVDGEILLKNAKRGTPRTLKWSRN-
STNCPLWVTSC-(168) (SEQ ID NO: 176), Npro R53E, G54D, R57E, P87L, A109S, C112E, V114S, V121N, T122A, C134E, C138E, L143E, I155S, F158S (1)MELNHFELLYKTSKQKPVGVEEPVYD-
TAGRPLFGNPSEVHPQSTLKLPHDRGEDDIE TTLRDL-
PRKGDCRSGNHLGPVSGIYIK-
PGLVYYQDYTGPVYHRAPLEFFDESQFEESTKR
IGRNAGSDGKLY-
HIYVEVDGEILLKEAKRGTPRTLKWSRN-
STNCPLWVTSC-(168) (SEQ ID NO: 177) and
Npro R53E, G54D, R57E, MOS, C112E, V114S, V121N,
C134E, C138E, L143Q, I155S, F158S
(1)MELNHFELLYKTSKQKPVGVEEPVYD-
TAGRPLFGNPSEVHPQSTLKLPHDRGEDDIE TTLRDL-
PRKGDCRSGNHLGPVSGIYIKPG-
PVYYQDYTGPVYHRAPLEFFDESQFEESTKR
IGRNTGSDGKLY-
HIYVEVDGEILLKQAKRGTPRTLKWSRN-
STNCPLWVTSC-(168) (SEQ ID NO: 178).

With such embodiments, target proteins may be provided in an immobilised functionally active form with "native like" structure, but of course without the risk of unwanted aggregation. Such immobilised or captured target proteins may be used for scientific studies, for immunological, intrinsic, fluorescence assays or for interaction assays with other physiological or pharmaceutically interesting molecules.

When necessary, because the cleavage rate might not be as high as desired, uncleaved fusion polypeptide that is washed off the column during the regeneration step can be re-fed into another circle of the chromatography process according to the present invention.

The liberated polypeptide of interest can be obtained optionally via choice of the respective buffers either in a partially or in a completely refolded state. Within the scope of the present invention, the polypeptide of interest in the effluent is either partially or preferably completely refolded. In one embodiment of the present invention, refolding of the autoproteolytic active part of the fusion polypeptide might be complete, while the polypeptide of interest remains partly unfolded. This situation can occur for example when the polypeptide of interest has a very complex conformation, for example a di- or trimerisation, or comprises a prosthetic group or a cofactor. Such polypeptide of interests might require particular conditions in order to complete refolding. Accordingly in such cases folding may be completed in a separate step, where special conditions, e.g. protonic strength and pH or the complete removal of detergents, which are usually added during refolding, can be generated.

Within the scope of the present invention, the conditions may be changed to any state where the fusion polypeptide stays adsorbed to the column.

The present invention also discloses oligopeptide ligands and derivatives of $N^{pro}$ of CSFV as described hereinabove for use according to the present invention. The present invention also relates to the use of an oligopeptide and a derivative of $N^{pro}$ of CSFV as described hereinabove according to the present invention.

According to another aspect, the present invention relates to the use of an affinity ligand as defined herein for affinity binding, especially for binding of autoprotease $N^{pro}$ of pestivirus ($N^{pro}$) or $N^{pro}$-mutants, and $N^{pro}$ fusion proteins.

Another aspect of the present invention relates to the affinity ligands or affinity matrices for binding of autoprotease $N^{pro}$ of pestivirus ($N^{pro}$) or $N^{pro}$-mutants, and $N^{pro}$ fusion proteins expressed as inclusion bodies under denaturing conditions, preferably the ligands as generally defined above under a) and b), especially the specific embodiments of these oligopeptides listed above; or affinity matrices for binding of autoprotease $N^{pro}$ of pestivirus ($N^{pro}$) or $N^{pro}$-mutants, and $N^{pro}$ fusion proteins expressed as inclusion bodies under denaturing conditions, preferably the matrices as generally defined herein.

The present invention is described further with reference to the following examples, which are illustrative only and non-limiting. In particular, the examples relate to preferred embodiments of the present invention.

EXAMPLES

Example 1

Affinity Chromatography 1.1.1 Chromatography Equipment

The chromatography runs in example 1 are performed on an ÄKTA 100 Explorer chromatography system (Amersham Biosciences). The prepared peptide affinity sorbents are packed into HR 5 columns (5 mm i.d., Amersham Biosciences). The gel volume is approximately 1 ml.

1.1.2 Preparation of Oligopeptide Ligands

The oligopeptide ligands used in example 1 are produced in the following way:

Solid Phase Peptide Synthesis is performed on a 433A peptide synthesizer (Applied Biosystems, Vienna, Austria) with 1-hydroxy-1H-benzotriazol/N,N'-dicyclohexylcarbodiimide (HOBt/DCC)-activation of Fmoc-protected amino acids (Bachem, Bubendorf, Switzerland). Peptides are synthesized on a 4-hydroxymethyl-phenoxymethyl-copolystyrene-1% divinylbenzene resin (HMP resin, Wang resin). Protecting groups for side chains are tert-butyl (t-Bu) for tyrosine, serine and threonine, OtBu for glutamic acid and aspartic acid, tert-butoxycarbonyl (Boc) for lysine and tryptophane and trityl (Trt) for cystein, histidine, asparagine and glutamine. For the coupling of the first amino acid 4-dimethylaminopyridine (DMAP) is used as a catalyst. After coupling of the first amino acid, a capping step is accomplished by using benzoic anhydride. Deprotection of the Fmoc group is performed with 20% piperidin. Side chain deprotection and cleavage from the resin are carried out by reaction with a cleavage mixture containing 95% trifluoroacetic acid (TFA), 2.5% water and 2.5% triisopropylsilane (TIS). After washing with dichloromethane (DCM) the crude peptide is purified by repeated ether precipitation followed by lyophilization. The peptides are further purified by RP-HPLC on a Luna 15μ C18 (2) 250×21.2 mm column (Phenomenex, Torrence, Calif., USA) with P 3500 pumps (Amersham Biosciences, Uppsala, Sweden), using a linear gradient of 5-50% acetonitrile vs. water (0.1% TFA) at 30 ml/min. Purity is confirmed by analytical RP-HPLC with a HP 1090 liquid chromatograph (Hewlett Packard, USA) using a Luna 3μ C18 (2) 100×4.6 mm column (Phenomenex) with a linear gradient of 1% acetonitrile per minute. Homogeneity and identity are verified by matrix assisted laser desorption ionization—time of flight mass spectrometry (ThermoBioanalysis, Hempstead, UK).

1.1.3 Preparation of Affinity Matrix

The affinity matrices used in example 1 are prepared in the following way:

10 g of Fractogel epoxy (M) (Merck, Darmstadt, Germany) is reacted with 50 ml 1 M Diaminodipropylamine (DADPA) for 48 hours at room temperature. After the reaction the gel is washed with a 50 ml 10 mM HCl and 3 times 50 ml water. The gel is resuspended in water, the pH is adjusted to 7.0 by addition of 0.1 M NaOH and 2 g of succinic anhydrid is added. After 30 minutes gentle stirring the pH is adjusted to 7.0 by addition of 10 M NaOH and another 2 g succinic anhydride are added. After another 30 minutes stirring the gel is washed with 50 ml 0.1 M NaOH, 50 ml phosphate buffered saline (PBS), 3 times with 50 ml water and 20% ethanol. After suction drying the gel is stored at 4° C.

1.1.4 Activation of the Carboxy-Group and Immobilization of Peptides:

The affinity matrices according to example 1 are activated in the following way:

1 g of wet Fractogel is modified with a DADPA-SA spacer as described in chapter 1.1.3 and washed 2 times with 5 ml Acetonitrile. Activation is perfomed with 3 ml 0.1 M Succinimidyl-trichloroethylcarbonate and 0.1 M triethylamine dissolved in acetonitrile for 3 hours. The gel is subsequently washed with acetonitrile and 1 mM HCl. The peptide AFYR-WYA (SEQ ID NO: 74) is dissolved in PBS at a concentration of 3 mg/ml. 5 ml of the peptide solution is rapidly added to the gel and reacted for 24 hours. The peptide VSFIWYK (SEQ ID NO: 117), is dissolved in dimethylformamide (DMF) containing 0.1 M triethylamine. 5 ml of the peptide solution are rapidly added to the gel and reacted for 24 hours. Coupling yield is determined by RP-HPLC of samples before and after coupling, Immobilization of Peptides on CIM-Epoxy:

Peptides are dissolved in a 100 mM $Na_2CO_3$ buffer pH 10.0 containing 0.15 M NaCl. The CIM-disks are mounted in a cartridge supplied by the manufacturer and the peptide solution is slowly pumped through the disk using a P1 pump (Amersham Biosciences) in a circulation mode for 48 hours at room temperature. Coupling yield is determined by RP-HPLC of samples before and after coupling. After coupling remaining epoxy groups are blocked with 0.5 M ethanolamine, pH 10.0 for 48 hours.

1.1.5 Expression of the Fusion Polypeptide

Recombinant E, coli HMS 174 (DE3) expressing a fusion polypeptide comprising the N-terminal autoprotease Npro with a 6×His-tag and a C-terminally fused GFPmut3.1 are cultured in a 10 l-fermenter. The fusion polypeptide comprises the following amino acid sequence (SEQ ID NO: 179):

it is possible routinely to operate at relatively high temperatures (for example 30° C. or 37° C.). The main culture is set up in a larger volume (for example 500 ml), where it is in particular necessary to ensure good aeration (large volume of flask compared with the volume of contents, high speed of rotation). Since it is intended that expression take place in the form of insoluble inclusion bodies, the main culture will in most cases also be carried out at relatively high temperature (for example 30 or 37° C.). Inducible systems are particularly suitable for producing inclusion bodies (for example with trp, lac, tac or phoA promoter). After the late logarithmic phase has been reached (usually at an optical density of 0.5 to 1.0 in shaken flasks), in these cases the inducer substance (for example indoleacrylic acid, isopropyl β-D-thiogalactopyranoside=IPTG) is added and incubation is continued for 1 to 5 hours. During this time, most of the $N^{pro}$ fusion polypeptide is deposited as inclusion bodies in the bacterial cytoplasm. The resulting cells can be harvested and processed further.

On a larger scale, the multistage system consists of a plurality of bioreactors (fermenters), it being preferred to employ defined nutrient media in this case in order to be able to improve the process engineering control of the process. In addition, it is possible greatly to increase biomass and product formation by metering in particular nutrients (fed batch). Otherwise, the process is analogous to the shaken flask. For example, a preliminary stage fermenter and a main stage fermenter are used, the cultivation temperature being chosen similar to that in the shaken flask. The preliminary stage fermenter is inoculated with a so called inoculum which is generally grown from a single colony or a cryoculture in a shaken flask. Good aeration and a sufficient inducer concentration must also be ensured in the fermenter—and especially in the main stage thereof. The induction phase must, however, in some cases be made distinctly longer compared to the shaken flask. The resulting cells are once again delivered for further processing.

```
  1 MHHHHHHELN HFELLYKTSK QKPVGVEEPV YDTAGRPLFG NPSEVHPQST LKLPHDRGRG   60

61 DIRTTLRDLP RKGDCRSGNH LGPVSGIYIK PGPVYYQDYT GPVYHRAPLE FFDEAQFCEV  120

121 TKRIGRVTGS DGKLYHIYVC VDGCILLKLA KRGTPRTLKW IRNFTNCPLW VTSCSGTMRK  180

181 GEELFTGVVP ILVELDGDVN GHKFSVSGEG EGDATYGKLT LKFICTTGKL PVPWPTLVTT  240

241 FGYGVQCFAR YPDHMKQHDF FKSAMPEGYV QERTIFFKDD GNYKTRAEVK FEGDTLVNRI  300

301 ELKGIDFKED GNILGHKLEY NYNSHNVYIM ADKQKNGIKV NFKIRHNIED GSVQLADHYQ  360

361 QNTPIGDGPV LLPDNHYLST QSALSKDPNE KRDHMVLLEF VTAAGITHGM DELYK
```

The bacterial host cell, i.e. the expression strain, is cultivated in accordance with microbiological practice known per se. The strain is generally brought up starting from a single colony on a nutrient medium, but it is also possible to employ cryopreserved cell suspensions (cell banks). The strain is generally cultivated in a multistage process in order to obtain sufficient biomass for further use.

On a small scale, this can take place in shaken flasks, it being possible in most cases to employ a complex medium (for example LB broth). However, it is also possible to use defined media (for example citrate medium). For the cultivation, a smallvolume pre-culture of the host strain (inoculated with a single colony or with cell suspension from a cryoculture) is grown, the temperature for this cultivation not generally being critical for the later expression result, so that 1.1.6 Isolation of Inclusion Bodies After harvesting, the cells (850 g wet weight) are suspended in 2500 ml of 50 mM Tris/HCl, 5 mM EDTA, 1% Triton X-100, pH 8.0. The chilled suspension is passed through an APV-2000 high pressure homogenizer (Invensys) for three times at 800 bar to disrupt the cells. Between the passages the suspension is chilled on ice and homogenized using an Ultraturrax. The homogenate is centrifuged at low speed (JLA 10.500, 7500 rpm, 30 min) to obtain the inclusion bodies containing the recombinant fusion polypeptide.

1.1.7 Solubilization of Inclusion Bodies

The pellet is suspended in 50 mM Tris/HCl, 5 mM EDTA, 1% Triton X-100, pH 8.0 and centrifuged. This step is repeated. After a $H_2O$-washing step the pellet is suspended in $H_2O$. The obtained inclusion body-suspension is stored at −20° C. for further use. The inclusion body-suspension is diluted 1:5 with 50 mM Tris/HCl, 10 M urea, 50 mM DTT, pH 7.3 at room temperature. Insoluble components are removed by centrifugation. A polypeptide concentration of about 15 mg/ml is obtained. The polypeptide solution is diluted with 50 mM Tris/HCl, 100 mM NaCl, 4 M urea, pH 7.3 to reach a polypeptide concentration of about 2 mg/ml.

1.1.8 Binding of the Fusion Polypeptide to the Chromatographic Column 0.5 ml of the polypeptide solution is applied to a Fractogel-DADPA-SA-VSFIWYK (SEQ ID NO: 117) (0.5×5 cm) matrix, whereby preparation and coupling of the respective peptide is conducted as described above in 1.1.2 and 1.1.3. The column is equilibrated with 50 mM Tris/HCl, 100 mM NaCl, 4 M urea, pH 7.3 with a linear flow rate of 50 cm/h. The flow rate is increased to 150 cm/h after sample injection.

1.1.9 Washing Out of Unbound Contaminating Material

Unbound components are washed out with 5 column volumes of equilibration buffer. A buffer exchange to refolding buffer, specifically to 0.5 M Tris/HCl, 2 mM EDTA, 3% glycerol, 5 mM DTT, pH 7.3, is performed with 4.5 column volumes.

1.1.10 Refolding, Cleavage and Elution

After changing the conditions from chaotropic to cosmotropic, the fusion polypeptide is allowed to refold for 25 h on the chromatography resin by stopping the flow. The active autoprotease cleaves off the C-terminally fused GFPmut3.1. The subsequent elution with refolding buffer at a flow rate of 50 cm/h results in purified native GFPmut3.1, as is confirmed by fluorescence measurements and SDS-PAGE.

1.1.11 Regeneration

Regeneration of the chromatography resin is performed with 0.1 M NaOH at a flow rate of 50 cm/h.

Example 2

Preparation of Affinity Matrices 2.1 Preparation of a Peptide Affinity Matrix with Coupling Through C-Terminal Lysine Derivatised with Iodoacetic Anhydride onto a Matrix with Thiol Groups (Fractogel-DADPA-IT).

300 mg of the N-acetylated peptide Ac-AFYRWYAK (SEQ ID NO: 128) was dissolved in 3 ml dimethylformamide (DMF) containing 65 µl diisopropylethyl-amine. The solution was then cooled on ice. Then 130 mg of iodoacetic anhydride were dissolved in 1.5 ml DMF and added to the peptide solution. The reaction was stopped after one minute by addition of 1 ml formic acid. The solution was then diluted with water to a final DMF concentration of 30%. The solution was then purified by preparative RP-HPLC as described before. Fractions were freeze-dried and analysed by mass spectrometry. 10 g Fractogel-DADPA was prepared as described above. The gel was subsequently washed 3 times with PBS buffer. The gel was then reacted with 10 mg/ml imminothiolan (IT) dissolved in PBS buffer for 2 hours. 250 mg of the peptide-iodoacetic acid-derivative was dissolved in 15 ml 20 mM MES buffer, pH 6.0 containing 30% of DMF. This solution was then reacted with the gel for 3 hours. Coupling yield was determined by analysing samples before and after coupling with RP-HPLC. Remaining thiol-groups on the gel were blocked with a 1 mg/ml iodoacetamide solution for 2 hours. The so prepared matrix is referred to as Fractogel-DADPA-IT-AFYRWYAK (SEQ ID NO: 180).

2.2 Preparation of an Affinity Matrix with Poly(Lysine, Tryptophane) Ligands 10 g Fractogel epoxy were washed 3 times with coupling buffer, a 20 mM sodium carbonate buffer, containing 150 mM sodium chloride and 10 mM triethylamine, pH 11.0. 100 mg of Poly(lysine, tryptophane), 4:1 (PolyKW, Sigma) were dissolved in 10 ml coupling buffer and reacted with the gel for 48 hours. Coupling efficiency was determined by measuring the absorbance at 280 nm of the Poly (lysine, tryptophane) solution before and after coupling. The gel was then reacted with 0.5 M ethanolamine to block remaining epoxy groups. The so prepared matrix is referred to as Fractogel-polyKW.

Alternatively the described procedure is carried out with Actigel B Ultraflow 4 epoxy. The so prepared matrix is referred to as Actigel-polyKW.

Furthermore the described procedure is carried out with Epoxy Sepharose 6B. The so prepared matrix is referred to as Sepharose-polyKW.

Example 3

Affinity Chromatography 3.1 Purification of NproEDDIE-6His Inclusion Body Extracts NproEDDIE-6His (SEQ ID NO: 181):

```
  1 MELNHFELLY KTSKQKPVGV EEPVYDTAGR PLFGNPSEVH PQSTLKLPHD RGEDDIETTL   60

61 RDLPRKGDCR SGNHLGPVSG IYIKPGPVYY QDYTGPVYHR APLEFFDETQ FEETTKRIGR  120

121 VTGSDGKLY HIYVEVDGEI LLKQAKRGTP RTLKWTRNTT NCPLWVTSCS VDKLAAALEH  180

181 HHRHH                                                             184
```

Crude NproEDDIE-6His inclusion body extracts in 50 mM Tris, 100 mM NaCl, 4 M urea, 10 mM α-monothioglycerol (MTG), pH 7.3 were loaded onto a Fractogel-DADPA-IT-AFYRWYAK (SEQ ID NO: 180) (0.5×5 cm) previously equilibrated with 50 mM Tris, 100 mM NaCl, 4 M urea, pH 7.3 at linear flow velocity of 25 and 150 cm/h respectively A sample amount of 5 ml at an approximate protein concentration of 2 mg/ml was applied. After wash out of unbound components with 5 column volumes (CV) of equilibration buffer at a linear flow velocity of 150 cm/h elution with 10 CV of 50 mM Tris, 1 M NaCl, 4 M urea, pH 7.3 was performed under same flow conditions. Regeneration of the column was performed with 10 CV of 0.2 M NaOH. Depletion of host cell compounds was confirmed by SDS-PAGE.

3.2 Purification of NproEDDIE-6His Inclusion Body Extracts

Crude NproEDDIE-6His inclusion body extracts in 50 mM Tris, 100 mM NaCl, 4 M urea, 10 mM MTG, pH 7.3 were loaded onto a Fractogel-poly-KW (0.5×5 cm) previously equilibrated with 50 mM Tris, 100 mM NaCl, 4 M urea, pH 7.3 at linear flow velocity of 25 and 150 cm/h respectively. A sample amount of 5 ml at an approximate protein concentration of 2 mg/ml was applied. After wash out of unbound components with 5 CV of equilibration buffer at a linear flow velocity of 150 cm/h elution with 10 CV of 50 mM Tris, 1 M NaCl, 8 M urea, pH 7.3 was performed under same flow conditions. Regeneration of the column was performed with 10 CV of 0.2 M NaOH. Depletion of host cell compounds was confirmed by SDS-PAGE.

3.3 Purification of NproEDDIE-6His Inclusion Body Extracts

Affinity chromatography of crude NproEDDIE-6His inclusion body extracts spiked with GFPmut3.1 producing *E. coli* HMS 174 (DE3) cell homogenate was performed on a Fractogel-DADPA-IT-AFYRWYAK (SEQ ID NO: 180) as described above. Samples of flow through and elution were collected and analysed for target protein and contaminant content by SDS-PAGE.

Example 4

Detection System

This detection system represents a generic detection system for Npro-EDDIE fusion proteins by means of a peptide ligand, which binds Npro-EDDIE, covalently immobilized or synthesized on a membrane. The fusion protein is bound to the membrane comprising the peptide and the fusion partner can be detected by its intrinsic features, e.g. autofluorescence of GFP, antibodies against the fusion partner, binding properties of the fusion partner. This membrane (as a preferred example of the affinity matrix according to the present invention) is specifically suitable for binding proteins which are not or only slightly soluble in aqueous solution and difficult to detect. Preferably, urea is used for solubilising such proteins according to the present invention.

In the case the autoprotease according to the present invention is used, the activity thereof may be inhibited by e.g. linkers, inactive mutants or inactivating buffers or buffer components (which may be added at the desired point in time.

Membranes with immobilized peptides AFR*WYA (SEQ ID NO: 182), where * represents each of the 20 proteinogenic amino acids, were incubated with crude 6×His-NproEDDIE-GFPmut3.1 inclusion body extracts at a concentration of 1 mg/ml in 50 mM Tris, 300 mM NaCl, 4 M urea, 12.5 mM dithiothreitol (DTT), pH 7.3 for 1 h. After 5 min wash with incubation buffer, conditions were changed to 1 M Tris, 0.25 M sucrose, 2 mM EDTA, 10 mM DTT, pH 7.3 to allow refolding of the fused GFPmut3.1. GFP fluorescence on peptide spots was detected with a Typhoon scanner (Amersham Biosciences) at an excitation wavelengh of 488 nm and emission at 520 nm at different photomultiplier voltages of 315, 350 and 400 V.

Example 5

Detection System with Biotinylated Anti-Npro-Peptide

This detection system represents a generic detection system for Npro-EDDIE fusion proteins by means of binding a biotinylated peptide to membrane-bound Npro-EDDIE fusion protein. The detection is carried out with a streptavidin-horseradish peroxidase-conjugate.

Over-expression of a fusion protein comprising Npro-EDDIE (SEQ ID NO: 124) and a C-terminally fused polypeptide in *E. coli* is detected by a labelled peptide directed against Npro-EDDIE (SEQ ID NO: 124): A cell homogenate is prepared by treatment of an *E. coli* fermentation broth with a solution containing 10 M urea. The homogenate is spotted on a nitrocellulose membrane. Afterwards the membrane is dried and blocked with 3% lysozyme in phosphate buffer for 1 hour. The membrane is then incubated with a solution containing 10 μg/ml of a AFYRWYAK (SEQ ID NO: 180)-Biotin-conjugate for 1 hour. Streptavidin-HPO dissolved in PBS containing 1 M sodium chloride is added for 15 min followed by 3 washes with incubation buffer and subsequent detection with Super Signal™ West Pico chemiluminescence detection system (Pierce, Rockford, Ill., USA) and Lumilmager™ (Boehringer, Mannheim, Germany).

Example 6

Preparation of Npro Mutant Fusion Proteins 10 ml of
- a fusion protein 6HisNPro-SGT-GFPmut 3.1 solution extracted from IBs as described above,
- 6HisNPro solution extracted from IBs as described above, and
- 6HisNPro-EDDIE (SEQ ID NO: 124) solution extracted from IBs as described above, were loaded onto
- a Fractogel-DADPA-SA-VSIFEW (SEQ ID NO: 56) column,
- a Fractogel-DADPA-SA-AVSIEWY (SEQ ID NO: 115) column,
- a Fractogel-DADPA-SA-AVSFIWY (SEQ ID NO: 116) column, and
- a Fractogel-DADPA-SA-VSFIWYK (SEQ ID NO: 117) column, each previously equilibrated with 50 mM Tris, 100 mM NaCl, 4 M urea buffer pH 7.3. After loading, the column was washed with 15 column volumes of equilibration buffer. Elution was carried out with an equilibration buffer added with 500 mM NaCl. Fractions collected during chromatography were analysed by SDS-PAGE. BSA and lysozyme are used as control proteins.

Preparation of Inclusion Bodies:

Recombinant *E. coli* HMS 174 (DE3) expressing a fusion protein comprising the N-terminal autoprotease $N^{pro}$ with a 6His-tag and GFPmut3.1 (see 1.1.5 above) were cultured in a 10 l-fermenter. After harvesting, the cells (850 g wet weight) were suspended in 2500 ml of 50 mM Tris, 5 mM EDTA, 1% Triton X-100, pH 8.0. The chilled suspension was passed through an APV-2000 high pressure homogenizer (Invensys) for three times at 800 bar to disrupt the cells. Between the passages the suspension was chilled on ice homogenized using an Ultraturrax. The homogenate was centrifuged at low speed (JLA 10.500, 7500 rpm, 30 mm) to obtain the inclusion bodies containing the recombinant fusion protein. The pellet was suspended in 50 mM Tris, 5 mM EDTA, 1% Triton X-100, pH and centrifuged. This step was repeated. After a $H_2O$-washing step the pellet was suspended in $H_2O$. 580 ml of an inclusion body-suspension with a dry mass of 8.9% were obtained and stored at −20° C. for further use. The inclusion body-suspension was diluted 1:5 with 50 mM Tris, 10 M urea, 50 mM DTT, pH 7.3 at RT. Insoluble components were removed by centrifugation. A protein concentration of about 15 mg/ml was obtained. The protein solution was diluted with 50 mM Tris, 100 mM NaCl, 4 M urea, pH 7.3 to reach a protein concentration of about 2 mg/ml.

The invention claimed is:

1. A method for affinity binding of a protein from a liquid starting preparation, wherein said protein is contacted under chaotropic conditions with an affinity matrix comprising a solid phase and an affinity ligand comprising peptide bonds coupled to said solid phase, wherein the affinity ligand is at least one member selected from the group of ligands consisting of:

AFYTWYA (SEQ ID NO: 71), AFYRWYA (SEQ ID NO: 74), AFFRWYA (SEQ ID NO: 75), AFGRWYA (SEQ ID NO: 76), AFHRWYA (SEQ ID NO: 77), AFIRWYA (SEQ ID NO: 78), AFLRWYA (SEQ ID NO: 79), AFMRWYA (SEQ ID NO: 80), AFNRWYA (SEQ ID NO: 81), AFPRWYA (SEQ ID NO: 82), AFQRWYA (SEQ ID NO: 83), AFRRWYA (SEQ ID NO: 84), AFSRWYA (SEQ ID NO: 85), AFTRWYA (SEQ ID NO: 86), AFVRWYA (SEQ ID NO: 87), AFYRWYA (SEQ ID NO: 88), AFYFWYA (SEQ ID NO: 89), AFYGWYA (SEQ ID NO: 90), AFYLWYA (SEQ ID NO: 91), AFYMWYA (SEQ ID NO: 92), AFYNWYA (SEQ ID NO: 93), AFYPWYA (SEQ ID NO: 94), AFYTWYA (SEQ ID NO: 95), AFYVWYA (SEQ ID NO: 96), AFYWWYA (SEQ ID NO: 97), AFYYWYA (SEQ ID NO: 98), Ac-AFYTWYAK (SEQ ID NO: 125), Ac-AFYRWYAK (SEQ ID NO: 128), Ac-AFFRWYAK (SEQ ID NO: 129), Ac-AFGRWYAK(SEQ ID NO: 130), Ac-AFHRWYAK (SEQ ID NO: 131), Ac-AFIRWYAK (SEQ ID NO: 132), Ac-AFLRWYAK (SEQ ID NO: 133), Ac-AFMRWYAK (SEQ ID NO: 134), Ac-AFNRWYAK (SEQ ID NO: 135), Ac-AFPRWYAK (SEQ ID NO: 136), Ac-AFQRWYAK (SEQ ID NO: 137), Ac-AFRRWYAK (SEQ ID NO: 138), Ac-AFSRWYAK (SEQ ID NO: 139), Ac-AFTRWYAK (SEQ ID NO: 140), Ac-AFVRWYAK (SEQ ID NO: 141), Ac-AFYFWYAK (SEQ ID NO: 142), Ac-AFYGWYAK (SEQ ID NO: 143), Ac-AFYLWYAK (SEQ ID NO: 144), Ac-AFYMWYAK (SEQ ID NO: 145), Ac-AFYNWYAK (SEQ ID NO: 146), Ac-AFYPWYAK (SEQ ID NO: 147), Ac-AFYTWYAK (SEQ ID NO: 148), Ac-AFYVWYAK (SEQ ID NO: 149), Ac-AFYWWYAK (SEQ ID NO: 150), and Ac-AFYYWYAK (SEQ ID NO: 151), whereby said protein binds to said matrix and is separated from said liquid starting preparation.

2. The method according to claim 1, wherein said protein bound to the matrix is further processed while being bound on said matrix.

3. The method according to claim 1, wherein said protein bound to the matrix or said processed protein is eluted from the matrix.

4. The method according to claim 1, wherein said protein is a heterologous recombinant polypeptide which comprises an autoproteolytic moiety and a moiety consisting of a protein of interest which is autoproteolytically cleaveable under non-chaotropic conditions by said autoproteolytic moiety, especially fusion proteins wherein the autoproteolytic moiety is autoprotease $N^{pro}$ of pestivirus ($N^{pro}$) or $N^{pro}$-mutants, and $N^{pro}$ fusion proteins expressed as inclusion bodies under denaturing conditions.

5. The method according to claim 4, wherein said autoproteolytic moiety is selected from the group consisting of

SEQ ID NO 1:
(1)-MELNHFELLYKTSKQKPVGVEEPVYDTAGRPLFGNPSEVHPQSTLK

LPHDRGRGDIRTTLRDLPRKGDCRSGNHLGPVSGIYIKPGPVYYQDYTGP

VYHRAPLEFFDEAQFCEVTKRIGRVTGSDGKLYHIYVCVDGCLLLKLAKR

GTPRTLKWIRNFTNCPLWVTSC-(168),

SEQ ID NO 2:
(1)-MELNHFELLYKTSKQKPVGVEEPVYDTAGRPLFGNPSEVHPQSTLK

LPHDRGRGDIRTTLRDLPRKGDCRSGNHLGPVSGIYIKPGPVYYQDYTGP

VYHRAPLEFFDEAQFEEVTKRIGRVTGSDGKLYHIYVEVDGEILLKLAKR

GTPRTLKWIRNFTNCPLWVTSC-(168),

SEQ ID NO 3:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDEAQFEEVTKRIGRVTGSDGKLYHIYVEVDGEILLKQAKR

GTPRTLKWIRNFTNCPLWVTSC-(168),

SEQ ID NO 4:
(1)-MELNHFELLYKTSKQKPVGVEEPVYDTAGRPLFGNPSEVHPQSTLK

LPHDRGRGDIRTTLRDLPRKGDCRSGNHLGPVSGIYIKPGPVYYQDYTGP

VYHRAPLEFFDETQFEETTKRIGRVTGSDGKLYHIYVEVDGEILLKLAKR

GTPRTLKWTRNTTNCPLWVTSC-(168),

SEQ ID NO 5:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDETQFEETTKRIGRVTGSDGKLYHIYVEVDGEILLKQAKR

GTPRTLKWTRNTTNCPLWVTSC-(168),

SEQ ID NO 6:
(1)-MELNHFELLYKTSKQKPVGVEEPVYDTAGRPLFGTPSEVHPQSTLK

LPHDRGEDDIETTLRDLPRKGDCRSGNHLGPVSGIYIKPGPVYYQDYTGP

VYHRAPLEFFDETQFEETTKRIGRVTGSDGKLYHIYVEVDGEILLKQAKR

GTPRTLKWTRNSTNCPLWVTSC-(168),

SEQ ID NO 7:
(1)-MELNHFELLYKTSKQKPVGVEEPVYDTEGRPLFGTPSEVHPQSTLK

LPHDRGEDDIETTLRDLPRKGDCRFGNHGPVSGIYIKPGPVYYQDYTGPV

YHRAPLEFFDETQFEETFFKRIGRVTGSDGKLYHIYVEVDGEILLKQAKR

GTPHTLKWTRNSTNCPLWVTSC-(168),

SEQ ID 8:
(1)-MELNHFELLYKTSKQKPVGVEEPVYDTAGRPLFGNPSEVHPQSTLK

LPHDRGEDDIETTLRDLPRKGDCRSGNHLGPVSGIYIKPGPVYYQDYTGP

VYHRAPLEFFDESQFEESTKRIGRVTGSDGKLYHIYVEVDGEILLKSAKR

GTPRTLKWSRNSTNCPLWVTSC-(168)
and

SEQ ID 9:
(1)-MELNHFELLYKTSKQKPVGVEEPVYDTAGRPLFGTPSEVHPQSTLK

LPHDRGRGDIRTTLRDLPRKGDCRSGNHLGPVSGIYIKPGPVYYQDYTGP

VYHRAPLEFFDEAQFCEVTKRIGRVTGSDGKLYHIYVCVDGCILLKLAKR

GTPRTLKWRNSTNCPLWVTSC-(168).

6. The method according to claim 1, wherein said protein is or comprises a protein or protein moiety which has a high tendency to aggregate under physiological conditions, especially a protein selected from the group consisting of Aβ peptides, Tau Prion protein, a-synuclein, Tau, ADan peptide, ABri peptide, Cystatin C, Superoxide dismutase, Atrophin 1, Huntingtin, Ataxins, Androgen receptor, TATA box-binding protein, Ig light chains, Serum amyloid A, Transthyretin, Transthyretin, β2-microglobulin, Apolipoprotein A-1, Gelsolin, Pro-islet amyloid polypeptide, Procalcitonin, Atrial natriuretic factor, Lysozyme, Insulin, Fibrinogen, full-length proteins or specific fragments, mutants, variants or polyQ-expansions thereof.

7. A method for affinity binding of a protein from a liquid starting preparation, wherein said protein is contacted under chaotropic conditions with an affinity matrix comprising a solid phase and an affinity ligand comprising peptide bonds coupled to said solid phase, wherein the affinity ligand is AFYRWYA (SEQ ID NO: 74).

8. The method according to claim 7, wherein said protein is or comprises a protein or protein moiety which has a high tendency to aggregate under physiological conditions, especially a protein selected from the group consisting of Aβ peptides, Tau Prion protein, a-synuclein, Tau, ADan peptide, ABri peptide, Cystatin C, Superoxide dismutase, Atrophin 1, Huntingtin, Ataxins, Androgen receptor, TATA box-binding protein, Ig light chains, Serum amyloid A, Transthyretin, Transthyretin, β2-microglobulin, Apolipoprotein A-1, Gelsolin, Pro-islet amyloid polypeptide, Procalcitonin, Atrial natriuretic factor, Lysozyme, Insulin, Fibrinogen, full-length proteins or specific fragments, mutants, variants or polyQ-expansions thereof.

* * * * *

SEQUENCE LISTING

<160> NUMBER OF SEQ ID NOS: 183

<210> SEQ ID NO 1
<211> LENGTH: 168
<212> TYPE: PRT
<213> ORGANISM: pestivirus

<400> SEQUENCE: 1

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 2
<211> LENGTH: 168
<212> TYPE: PRT
<213> ORGANISM: Artificial Sequence
<220> FEATURE:
<223> OTHER INFORMATION: Synthetic modified autoprotease Npro of
      classical swine fever virus

<400> SEQUENCE: 2

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Glu
            100                 105                 110

Glu Val Thr Lys Arg Ile Gly Arg Val Thr Gly Ser Asp Gly Lys Leu
        115                 120                 125

```
Tyr His Ile Tyr Val Glu Val Asp Gly Glu Ile Leu Leu Lys Leu Ala
        130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 3
<211> LENGTH: 168
<212> TYPE: PRT
<213> ORGANISM: Artificial Sequence
<220> FEATURE:
<223> OTHER INFORMATION: Synthetic modified autoprotease Npro of
      classical swine fever virus

<400> SEQUENCE: 3

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Glu
            100                 105                 110

Glu Val Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 4
<211> LENGTH: 168
<212> TYPE: PRT
<213> ORGANISM: Artificial Sequence
<220> FEATURE:
<223> OTHER INFORMATION: Synthetic modified autoprotease Npro of
      classical swine fever virus

<400> SEQUENCE: 4

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
```

```
                    85                  90                  95
Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys Leu Ala
            130                 135                 140

Lys Arg Gly Thr Pro Arg Thr Leu Lys Trp Thr Arg Asn Thr Thr Asn
145                 150                 155                 160

Cys Pro Leu Trp Val Thr Ser Cys
                165

<210> SEQ ID NO 5
<211> LENGTH: 168
<212> TYPE: PRT
<213> ORGANISM: Artificial Sequence
<220> FEATURE:
<223> OTHER INFORMATION: Synthetic modified autoprotease Npro of
      classical swine fever virus

<400> SEQUENCE: 5

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys Gln Ala
            130                 135                 140

Lys Arg Gly Thr Pro Arg Thr Leu Lys Trp Thr Arg Asn Thr Thr Asn
145                 150                 155                 160

Cys Pro Leu Trp Val Thr Ser Cys
                165

<210> SEQ ID NO 6
<211> LENGTH: 168
<212> TYPE: PRT
<213> ORGANISM: Artificial Sequence
<220> FEATURE:
<223> OTHER INFORMATION: Synthetic modified autoprotease Npro of
      classical swine fever virus

<400> SEQUENCE: 6

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Thr Pro Ser Glu Val His Pro Gln Ser Thr Leu Lys Leu Pro
        35                  40                  45
```

```
His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
 65                  70                  75                  80

Ile Tyr Ile Lys Pro Gly Pro Val Tyr Tyr Gln Asp Tyr Thr Gly Pro
                 85                  90                  95

Val Tyr His Arg Ala Pro Leu Glu Phe Phe Asp Glu Thr Gln Phe Glu
                100                 105                 110

Glu Thr Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys Gln Ala
        130                 135                 140

Lys Arg Gly Thr Pro Arg Thr Leu Lys Trp Thr Arg Asn Ser Thr Asn
145                 150                 155                 160

Cys Pro Leu Trp Val Thr Ser Cys
                165
```

```
<210> SEQ ID NO 7
<211> LENGTH: 168
<212> TYPE: PRT
<213> ORGANISM: Artificial Sequence
<220> FEATURE:
<223> OTHER INFORMATION: Synthetic modified autoprotease Npro of
      classical swine fever virus

<400> SEQUENCE: 7
```

```
Met Glu Leu Asn His Phe Glu Leu Leu Tyr Lys Thr Ser Lys Gln Lys
 1               5                  10                  15

Pro Val Gly Val Glu Glu Pro Val Tyr Asp Thr Glu Gly Arg Pro Leu
                20                  25                  30

Phe Gly Thr Pro Ser Glu Val His Pro Gln Ser Thr Leu Lys Leu Pro
            35                  40                  45

His Asp Arg Gly Glu Asp Asp Ile Glu Thr Thr Leu Arg Asp Leu Pro
    50                  55                  60

Arg Lys Gly Asp Cys Arg Phe Gly Asn His Leu Gly Pro Val Ser Gly
 65                  70                  75                  80

Ile Tyr Ile Lys Pro Gly Pro Val Tyr Tyr Gln Asp Tyr Thr Gly Pro
                 85                  90                  95

Val Tyr His Arg Ala Pro Leu Glu Phe Phe Asp Glu Thr Gln Phe Glu
                100                 105                 110

Glu Thr Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys Gln Ala
        130                 135                 140

Lys Arg Gly Thr Pro His Thr Leu Lys Trp Thr Arg Asn Ser Thr Asn
145                 150                 155                 160

Cys Pro Leu Trp Val Thr Ser Cys
                165
```

```
<210> SEQ ID NO 8
<211> LENGTH: 168
<212> TYPE: PRT
<213> ORGANISM: Artificial Sequence
<220> FEATURE:
<223> OTHER INFORMATION: Synthetic modified autoprotease Npro of
      classical swine fever virus

<400> SEQUENCE: 8
```

```
Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
            35                  40                  45

His Asp Arg Gly Glu Asp Ile Glu Thr Thr Leu Arg Asp Leu Pro
        50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Gln Asp Tyr Thr Gly Pro
                85                  90                  95

Val Tyr His Arg Ala Pro Leu Glu Phe Phe Asp Glu Ser Gln Phe Glu
            100                 105                 110

Glu Ser Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys Ser Ala
        130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
                165

<210> SEQ ID NO 9
<211> LENGTH: 168
<212> TYPE: PRT
<213> ORGANISM: Artificial Sequence
<220> FEATURE:
<223> OTHER INFORMATION: Synthetic modified autoprotease Npro of
      classical swine fever virus

<400> SEQUENCE: 9

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Thr Pro Ser Glu Val His Pro Gln Ser Thr Leu Lys Leu Pro
            35                  40                  45

His Asp Arg Gly Arg Gly Asp Ile Arg Thr Thr Leu Arg Asp Leu Pro
        50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
            115                 120                 125

Tyr His Ile Tyr Val Cys Val Asp Gly Cys Ile Leu Leu Lys Leu Ala
        130                 135                 140

Lys Arg Gly Thr Pro Arg Thr Leu Lys Trp Ile Arg Asn Ser Thr Asn
145                 150                 155                 160

Cys Pro Leu Trp Val Thr Ser Cys
                165

<210> SEQ ID NO 10
<211> LENGTH: 415
```

```
<212> TYPE: PRT
<213> ORGANISM: Artificial Sequence
<220> FEATURE:
<223> OTHER INFORMATION: Synthetic fusion protein comprising
      autoprotease Npro of classical swine fever virus

<400> SEQUENCE: 10

Met His His His His His Glu Leu Asn His Phe Glu Leu Leu Tyr
1               5                   10                  15

Lys Thr Ser Lys Gln Lys Pro Val Gly Val Glu Glu Pro Val Tyr Asp
                20                  25                  30

Thr Ala Gly Arg Pro Leu Phe Gly Asn Pro Ser Glu Val His Pro Gln
            35                  40                  45

Ser Thr Leu Lys Leu Pro His Asp Arg Gly Arg Gly Asp Ile Arg Thr
        50                  55                  60

Thr Leu Arg Asp Leu Pro Arg Lys Gly Asp Cys Arg Ser Gly Asn His
65                  70                  75                  80

Leu Gly Pro Val Ser Gly Ile Tyr Ile Lys Pro Gly Pro Val Tyr Tyr
                85                  90                  95

Gln Asp Tyr Thr Gly Pro Val Tyr His Arg Ala Pro Leu Glu Phe Phe
                100                 105                 110

Asp Glu Ala Gln Phe Cys Glu Val Thr Lys Arg Ile Gly Arg Val Thr
            115                 120                 125

Gly Ser Asp Gly Lys Leu Tyr His Ile Tyr Val Cys Val Asp Gly Cys
130                 135                 140

Ile Leu Leu Lys Leu Ala Lys Arg Gly Thr Pro Arg Thr Leu Lys Trp
145                 150                 155                 160

Ile Arg Asn Phe Thr Asn Cys Pro Leu Trp Val Thr Ser Cys Ser Gly
                165                 170                 175

Thr Met Arg Lys Gly Glu Glu Leu Phe Thr Gly Val Val Pro Ile Leu
                180                 185                 190

Val Glu Leu Asp Gly Asp Val Asn Gly His Lys Phe Ser Val Ser Gly
            195                 200                 205

Glu Gly Glu Gly Asp Ala Thr Tyr Gly Lys Leu Thr Leu Lys Phe Ile
210                 215                 220

Cys Thr Thr Gly Lys Leu Pro Val Pro Trp Pro Thr Leu Val Thr Thr
225                 230                 235                 240

Phe Gly Tyr Gly Val Gln Cys Phe Ala Arg Tyr Pro Asp His Met Lys
                245                 250                 255

Gln His Asp Phe Phe Lys Ser Ala Met Pro Glu Gly Tyr Val Gln Glu
                260                 265                 270

Arg Thr Ile Phe Phe Lys Asp Asp Gly Asn Tyr Lys Thr Arg Ala Glu
            275                 280                 285

Val Lys Phe Glu Gly Asp Thr Leu Val Asn Arg Ile Glu Leu Lys Gly
290                 295                 300

Ile Asp Phe Lys Glu Asp Gly Asn Ile Leu Gly His Lys Leu Glu Tyr
305                 310                 315                 320

Asn Tyr Asn Ser His Asn Val Tyr Ile Met Ala Asp Lys Gln Lys Asn
                325                 330                 335

Gly Ile Lys Val Asn Phe Lys Ile Arg His Asn Ile Glu Asp Gly Ser
                340                 345                 350

Val Gln Leu Ala Asp His Tyr Gln Gln Asn Thr Pro Ile Gly Asp Gly
            355                 360                 365

Pro Val Leu Leu Pro Asp Asn His Tyr Leu Ser Thr Gln Ser Ala Leu
370                 375                 380
```

```
Ser Lys Asp Pro Asn Glu Lys Arg Asp His Met Val Leu Leu Glu Phe
385                 390                 395                 400

Val Thr Ala Ala Gly Ile Thr His Gly Met Asp Glu Leu Tyr Lys
                405                 410                 415

<210> SEQ ID NO 11
<211> LENGTH: 184
<212> TYPE: PRT
<213> ORGANISM: Artificial Sequence
<220> FEATURE:
<223> OTHER INFORMATION: Synthetic fusion protein comprising
      autoprotease Npro of classical swine fever virus

<400> SEQUENCE: 11

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro Arg Thr Leu Lys Trp Thr Arg Asn Thr Thr Asn
145                 150                 155                 160

Cys Pro Leu Trp Val Thr Ser Cys Ser Val Asp Lys Leu Ala Ala Ala
                165                 170                 175

Leu Glu His His His His His His
            180

<210> SEQ ID NO 12
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 12

Val Ser Asp Asp Trp Tyr
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 13

Val Ser Glu Asp Trp Tyr
1               5
```

-continued

```
<210> SEQ ID NO 14
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 14

Val Ser Ile Asp Trp Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 15

Val Ser Tyr Asp Trp Tyr
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 16

Val Ser Val Asp Trp Tyr
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 17

Val Ser Trp Asp Trp Tyr
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 18

Val Ser Tyr Asp Trp Tyr
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 19

Val Ser Phe Asp Trp Tyr
1               5

<210> SEQ ID NO 20
<211> LENGTH: 6
```

```
<212> TYPE: PRT
<213> ORGANISM: Artificial Sequence
<220> FEATURE:
<223> OTHER INFORMATION: Synthetic affinity ligand

<400> SEQUENCE: 20

Val Ser Asp Glu Trp Tyr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 21

Val Ser Glu Glu Trp Tyr
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 22

Val Ser Ile Glu Trp Tyr
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 23

Val Ser Tyr Glu Trp Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 24

Val Ser Val Glu Trp Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 25

Val Ser Trp Glu Trp Tyr
1               5

<210> SEQ ID NO 26
<211> LENGTH: 6
<212> TYPE: PRT
<213> ORGANISM: Artificial Sequence
```

```
<220> FEATURE:
<223> OTHER INFORMATION: Synthetic affinity ligand

<400> SEQUENCE: 26

Val Ser Tyr Glu Trp Tyr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 27

Val Ser Phe Glu Trp Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 28

Asp Asp Asp Asp Trp Tyr
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 29

Asp Asp Glu Asp Trp Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 30

Asp Asp Ile Asp Trp Tyr
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 31

Asp Asp Tyr Asp Trp Tyr
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic affinity ligand
```

```
<400> SEQUENCE: 32

Asp Asp Val Asp Trp Tyr
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 33

Asp Asp Trp Asp Trp Tyr
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 34

Asp Asp Tyr Asp Trp Tyr
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 35

Asp Asp Phe Asp Trp Tyr
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 36

Val Ser Ile Phe Trp Glu
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 37

Phe Ser Ile Phe Glu Trp
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 38
```

```
Trp Ser Ile Phe Glu Trp
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 39

Val Ser Leu Ile Trp Tyr
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 40

Val Ser Leu Ile Asp Trp
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 41

Val Ser Leu Ile Glu Trp
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 42

Val Ser Leu Ile Trp Glu
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 43

Phe Ser Leu Glu Glu Trp
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 44

Val Ser Asp Leu Asp Trp
```

```
<210> SEQ ID NO 45
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 45

Val Ser Asp Leu Glu Trp
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 46

Val Ser Tyr Ile Asp Trp
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 47

Val Ser Tyr Ile Trp Glu
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 48

Val Ser Ile Asp Trp Tyr
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 49

Val Ser Ile Glu Trp Tyr
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 50

Val Ser Ile Trp Trp Tyr
1               5
```

```
<210> SEQ ID NO 51
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 51

Val Ser Ile Ile Trp Tyr
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 52

Val Ser Tyr Ile Trp Tyr
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 53

Val Ser Val Ile Trp Tyr
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 54

Val Ser Phe Ile Trp Tyr
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 55

Val Ser Phe Ile Trp Glu
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 56

Val Ser Ile Phe Glu Trp
1               5

<210> SEQ ID NO 57
```

```
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 57

Val Ser Ile Phe Trp Glu
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 58

Phe Ser Ile Phe Glu Trp
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 59

Trp Ser Ile Phe Glu Trp
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 60

Val Ser Leu Ile Trp Tyr
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 61

Val Ser Leu Ile Asp Trp
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 62

Val Ser Leu Ile Glu Trp
1               5

<210> SEQ ID NO 63
<211> LENGTH: 6
<212> TYPE: PRT
```

```
<213> ORGANISM: Artificial Sequence
<220> FEATURE:
<223> OTHER INFORMATION: Synthetic affinity ligand

<400> SEQUENCE: 63

Val Ser Leu Ile Trp Glu
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 64

Phe Ser Leu Ile Glu Trp
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 65

Trp Ser Leu Ile Glu Trp
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 66

Phe Ser Tyr Phe Glu Trp
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 67

Phe Ser Phe Tyr Glu Trp
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 68

Trp Ser Phe Tyr Glu Trp
1               5

<210> SEQ ID NO 69
<211> LENGTH: 6
<212> TYPE: PRT
<213> ORGANISM: Artificial Sequence
<220> FEATURE:
```

```
<223> OTHER INFORMATION: Synthetic affinity ligand

<400> SEQUENCE: 69

Phe Ser Tyr Ile Glu Trp
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 70

Trp Ser Tyr Ile Glu Trp
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 71

Ala Phe Tyr Thr Trp Tyr Ala
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 72

Ala Phe Tyr Arg Trp Tyr Lys
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic affinity ligand

<400> SEQUENCE: 73

Ala Phe Tyr Arg Trp Tyr
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 74

Ala Phe Tyr Arg Trp Tyr Ala
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic affinity ligand
```

```
<400> SEQUENCE: 75

Ala Phe Phe Arg Trp Tyr Ala
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 76

Ala Phe Gly Arg Trp Tyr Ala
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 77

Ala Phe His Arg Trp Tyr Ala
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 78

Ala Phe Ile Arg Trp Tyr Ala
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 79

Ala Phe Leu Arg Trp Tyr Ala
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 80

Ala Phe Met Arg Trp Tyr Ala
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 81
```

Ala Phe Asn Arg Trp Tyr Ala
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 82

Ala Phe Pro Arg Trp Tyr Ala
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 83

Ala Phe Gln Arg Trp Tyr Ala
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 84

Ala Phe Arg Arg Trp Tyr Ala
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 85

Ala Phe Ser Arg Trp Tyr Ala
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 86

Ala Phe Thr Arg Trp Tyr Ala
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 87

Ala Phe Val Arg Trp Tyr Ala
1               5

```
<210> SEQ ID NO 88
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 88

Ala Phe Tyr Arg Trp Tyr Ala
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 89

Ala Phe Tyr Phe Trp Tyr Ala
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 90

Ala Phe Tyr Gly Trp Tyr Ala
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 91

Ala Phe Tyr Leu Trp Tyr Ala
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 92

Ala Phe Tyr Met Trp Tyr Ala
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 93

Ala Phe Tyr Asn Trp Tyr Ala
1               5
```

```
<210> SEQ ID NO 94
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 94

Ala Phe Tyr Pro Trp Tyr Ala
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 95

Ala Phe Tyr Thr Trp Tyr Ala
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 96

Ala Phe Tyr Val Trp Tyr Ala
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 97

Ala Phe Tyr Trp Trp Tyr Ala
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 98

Ala Phe Tyr Tyr Trp Tyr Ala
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 99

Ala Lys Trp Phe Arg Tyr Ala
1               5

<210> SEQ ID NO 100
<211> LENGTH: 6
```

```
<212> TYPE: PRT
<213> ORGANISM: Artificial Sequence
<220> FEATURE:
<223> OTHER INFORMATION: Synthetic affinity ligand

<400> SEQUENCE: 100

Val Ser Arg Asn Trp Tyr
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 101

Ala Ser Arg Asn Trp Tyr Ala
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 102

Ala Ser Arg Phe Trp Tyr Ala
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 103

Phe Ser Arg Asn Trp Tyr Ala
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 104

Val Phe Arg Asn Trp Tyr Ala
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 105

Val Trp Arg Asn Trp Tyr Ala
1               5

<210> SEQ ID NO 106
<211> LENGTH: 7
<212> TYPE: PRT
<213> ORGANISM: Artificial Sequence
```

```
<220> FEATURE:
<223> OTHER INFORMATION: Synthetic affinity ligand

<400> SEQUENCE: 106

Val Tyr Arg Asn Trp Tyr Ala
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 107

Val Ser Arg Ala Trp Tyr Ala
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 108

Val Ser Arg Phe Trp Tyr Ala
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 109

Val Ser Arg Trp Trp Tyr Ala
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 110

Val Ser Arg Tyr Trp Tyr Ala
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 111

Val Ser Arg Asn Phe Tyr Ala
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic affinity ligand
```

```
<400> SEQUENCE: 112

Val Ser Arg Asn Tyr Tyr Ala
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 113

Val Ser Arg Asn Trp Phe Ala
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic affinity ligand

<400> SEQUENCE: 114

Val Ser Arg Asn Trp Trp Ala
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic

<400> SEQUENCE: 115

Ala Val Ser Ile Glu Trp Tyr
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic

<400> SEQUENCE: 116

Ala Val Ser Phe Ile Trp Tyr
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic

<400> SEQUENCE: 117

Val Ser Phe Ile Trp Tyr Lys
1               5

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118
```

```
Ala Val Ser Ile Phe Glu Trp Tyr
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic

<400> SEQUENCE: 119

Ala Val Ser Arg Asn Trp Tyr
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic

<400> SEQUENCE: 120

Ala Ser Arg Phe Trp Tyr
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic

<400> SEQUENCE: 121

Ala Phe Tyr Arg Trp Tyr Ala Ala
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic

<400> SEQUENCE: 122

Ala Ser Arg Phe Trp Tyr Ala Ala
1               5

<210> SEQ ID NO 123
<211> LENGTH: 8
<212> TYPE: PRT
<213> ORGANISM: Artificial Sequence
<220> FEATURE:
<223> OTHER INFORMATION: Synthetic

<400> SEQUENCE: 123

Ala Phe Tyr Ser Trp Tyr Ala Ala
1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic

<400> SEQUENCE: 124

Glu Asp Asp Ile Glu
```

```
<210> SEQ ID NO 125
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 125

Ala Phe Tyr Thr Trp Tyr Ala Lys
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 126

Ala Phe Tyr Arg Trp Tyr Lys Lys
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 127

Ala Phe Tyr Arg Trp Tyr Lys
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 128

Ala Phe Tyr Arg Trp Tyr Ala Lys
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
```

```
<223> OTHER INFORMATION: ACETYLATION

<400> SEQUENCE: 129

Ala Phe Phe Arg Trp Tyr Ala Lys
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 130

Ala Phe Gly Arg Trp Tyr Ala Lys
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 131

Ala Phe His Arg Trp Tyr Ala Lys
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 132

Ala Phe Ile Arg Trp Tyr Ala Lys
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 133

Ala Phe Leu Arg Trp Tyr Ala Lys
1               5

<210> SEQ ID NO 134
<211> LENGTH: 8
<212> TYPE: PRT
<213> ORGANISM: Artificial Sequence
```

```
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 134

Ala Phe Met Arg Trp Tyr Ala Lys
1               5

<210> SEQ ID NO 135
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 135

Ala Phe Asn Arg Trp Tyr Ala Lys
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 136

Ala Phe Pro Arg Trp Tyr Ala Lys
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 137

Ala Phe Gln Arg Trp Tyr Ala Lys
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 138

Ala Phe Arg Arg Trp Tyr Ala Lys
1               5
```

```
<210> SEQ ID NO 139
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 139

Ala Phe Ser Arg Trp Tyr Ala Lys
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 140

Ala Phe Thr Arg Trp Tyr Ala Lys
1               5

<210> SEQ ID NO 141
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 141

Ala Phe Val Arg Trp Tyr Ala Lys
1               5

<210> SEQ ID NO 142
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 142

Ala Phe Tyr Phe Trp Tyr Ala Lys
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
```

```
<400> SEQUENCE: 143

Ala Phe Tyr Gly Trp Tyr Ala Lys
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 144

Ala Phe Tyr Leu Trp Tyr Ala Lys
1               5

<210> SEQ ID NO 145
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 145

Ala Phe Tyr Met Trp Tyr Ala Lys
1               5

<210> SEQ ID NO 146
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 146

Ala Phe Tyr Asn Trp Tyr Ala Lys
1               5

<210> SEQ ID NO 147
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 147

Ala Phe Tyr Pro Trp Tyr Ala Lys
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic
```

```
<220> FEATURE:
<221> NAME/KEY: MOD_RES
<222> LOCATION: (1)..(1)
<223> OTHER INFORMATION: ACETYLATION

<400> SEQUENCE: 148

Ala Phe Tyr Thr Trp Tyr Ala Lys
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 149

Ala Phe Tyr Val Trp Tyr Ala Lys
1               5

<210> SEQ ID NO 150
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 150

Ala Phe Tyr Trp Trp Tyr Ala Lys
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 151

Ala Phe Tyr Tyr Trp Tyr Ala Lys
1               5

<210> SEQ ID NO 152
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 152

Ala Lys Trp Phe Arg Tyr Ala Lys
1               5

<210> SEQ ID NO 153
```

```
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 153

Val Ser Arg Asn Trp Tyr Lys
1               5

<210> SEQ ID NO 154
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 154

Ala Ser Arg Asn Trp Tyr Ala Lys
1               5

<210> SEQ ID NO 155
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 155

Ala Ser Arg Phe Trp Tyr Ala Lys
1               5

<210> SEQ ID NO 156
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 156

Phe Ser Arg Asn Trp Tyr Ala Lys
1               5

<210> SEQ ID NO 157
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 157
```

```
Val Phe Arg Asn Trp Tyr Ala Lys
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 158

Val Trp Arg Asn Trp Tyr Ala Lys
1               5

<210> SEQ ID NO 159
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 159

Val Tyr Arg Asn Trp Tyr Ala Lys
1               5

<210> SEQ ID NO 160
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 160

Val Ser Arg Ala Trp Tyr Ala Lys
1               5

<210> SEQ ID NO 161
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 161

Val Ser Arg Phe Trp Tyr Ala Lys
1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
```

```
<222> LOCATION: (1)..(1)
<223> OTHER INFORMATION: ACETYLATION

<400> SEQUENCE: 162

Val Ser Arg Trp Trp Tyr Ala Lys
1               5

<210> SEQ ID NO 163
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 163

Val Ser Arg Tyr Trp Tyr Ala Lys
1               5

<210> SEQ ID NO 164
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 164

Val Ser Arg Asn Phe Tyr Ala Lys
1               5

<210> SEQ ID NO 165
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 165

Val Ser Arg Asn Tyr Tyr Ala Lys
1               5

<210> SEQ ID NO 166
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 166

Val Ser Arg Asn Trp Phe Ala Lys
1               5

<210> SEQ ID NO 167
<211> LENGTH: 8
<212> TYPE: PRT
```

```
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 167

Val Ser Arg Asn Trp Trp Ala Lys
1               5

<210> SEQ ID NO 168
<211> LENGTH: 4
<212> TYPE: PRT
<213> ORGANISM: Artificial Sequence
<220> FEATURE:
<223> OTHER INFORMATION: Synthetic

<400> SEQUENCE: 168

Tyr Trp Lys Ala
1

<210> SEQ ID NO 169
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 169

Tyr Trp Lys Ala Lys
1               5

<210> SEQ ID NO 170
<211> LENGTH: 4
<212> TYPE: PRT
<213> ORGANISM: Artificial Sequence
<220> FEATURE:
<223> OTHER INFORMATION: Synthetic

<400> SEQUENCE: 170

Tyr Lys Tyr Ala
1

<210> SEQ ID NO 171
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 171

Tyr Lys Tyr Ala Lys
1               5

<210> SEQ ID NO 172
<211> LENGTH: 4
<212> TYPE: PRT
<213> ORGANISM: Artificial Sequence
<220> FEATURE:
<223> OTHER INFORMATION: Synthetic
```

<400> SEQUENCE: 172

Tyr Trp Arg Ala
1

<210> SEQ ID NO 173
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 173

Tyr Trp Arg Ala Lys
1               5

<210> SEQ ID NO 174
<211> LENGTH: 4
<212> TYPE: PRT
<213> ORGANISM: Artificial Sequence
<220> FEATURE:
<223> OTHER INFORMATION: Synthetic

<400> SEQUENCE: 174

Ala Arg Trp Tyr
1

<210> SEQ ID NO 175
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 175

Ala Arg Trp Tyr Lys
1               5

<210> SEQ ID NO 176
<211> LENGTH: 168
<212> TYPE: PRT
<213> ORGANISM: Artificial Sequence
<220> FEATURE:
<223> OTHER INFORMATION: Synthetic

<400> SEQUENCE: 176

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Met Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asn Tyr Thr Gly Pro
                85                  90                  95

Val Tyr His Arg Ala Pro Leu Glu Phe Phe Asp Glu Ser Gln Phe Glu
            100                 105                 110

Glu Ser Thr Lys Arg Ile Gly Arg Val Thr Gly Ser Asp Gly Lys Leu
            115                 120                 125

Tyr His Ile Tyr Val Glu Val Asp Gly Glu Ile Leu Leu Lys Asn Ala
        130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
            165

<210> SEQ ID NO 177
<211> LENGTH: 168
<212> TYPE: PRT
<213> ORGANISM: Artificial Sequence
<220> FEATURE:
<223> OTHER INFORMATION: Synthetic

<400> SEQUENCE: 177

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Leu Val Tyr Tyr Gln Asp Tyr Thr Gly Pro
                85                  90                  95

Val Tyr His Arg Ala Pro Leu Glu Phe Phe Asp Glu Ser Gln Phe Glu
            100                 105                 110

Glu Ser Thr Lys Arg Ile Gly Arg Asn Ala Gly Ser Asp Gly Lys Leu
            115                 120                 125

Tyr His Ile Tyr Val Glu Val Asp Gly Glu Ile Leu Leu Lys Glu Ala
        130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
            165

<210> SEQ ID NO 178
<211> LENGTH: 168
<212> TYPE: PRT
<213> ORGANISM: Artificial Sequence
<220> FEATURE:
<223> OTHER INFORMATION: Synthetic

<400> SEQUENCE: 178

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Asp Ile Glu Thr Thr Leu Arg Asp Leu Pro
    50                  55                  60

```
Arg Lys Gly Asp Cys Arg Ser Gly Asn His Leu Gly Pro Val Ser Gly
 65                  70                  75                  80

Ile Tyr Ile Lys Pro Gly Pro Val Tyr Tyr Gln Asp Tyr Thr Gly Pro
                 85                  90                  95

Val Tyr His Arg Ala Pro Leu Glu Phe Phe Asp Glu Ser Gln Phe Glu
            100                 105                 110

Glu Ser Thr Lys Arg Ile Gly Arg Asn Thr Gly Ser Asp Gly Lys Leu
                115                 120                 125

Tyr His Ile Tyr Val Glu Val Asp Gly Glu Ile Leu Leu Lys Gln Ala
            130                 135                 140

Lys Arg Gly Thr Pro Arg Thr Leu Lys Trp Ser Arg Asn Ser Thr Asn
145                 150                 155                 160

Cys Pro Leu Trp Val Thr Ser Cys
                165
```

```
<210> SEQ ID NO 179
<211> LENGTH: 414
<212> TYPE: PRT
<213> ORGANISM: Artificial Sequence
<220> FEATURE:
<223> OTHER INFORMATION: Synthetic

<400> SEQUENCE: 179

Met His His His His His Glu Leu Asn His Phe Glu Leu Leu Tyr
 1               5                  10                  15

Lys Thr Ser Lys Gln Lys Pro Val Gly Val Glu Glu Pro Val Tyr Asp
                 20                  25                  30

Thr Ala Gly Arg Pro Leu Phe Gly Asn Pro Ser Glu Val His Pro Gln
             35                  40                  45

Ser Thr Leu Lys Leu Pro His Asp Arg Gly Arg Gly Asp Ile Arg Thr
 50                  55                  60

Thr Leu Arg Asp Leu Pro Arg Lys Gly Asp Cys Arg Ser Gly Asn His
 65                  70                  75                  80

Leu Gly Pro Val Ser Gly Ile Tyr Ile Lys Pro Gly Pro Val Tyr Tyr
                 85                  90                  95

Gln Asp Tyr Thr Gly Pro Val Tyr His Arg Ala Pro Leu Glu Phe Phe
            100                 105                 110

Asp Glu Ala Gln Phe Cys Glu Val Thr Lys Arg Ile Gly Arg Val Thr
            115                 120                 125

Gly Ser Asp Gly Lys Leu Tyr His Ile Tyr Val Cys Val Asp Gly Cys
130                 135                 140

Ile Leu Leu Lys Leu Ala Lys Arg Gly Thr Pro Arg Thr Leu Lys Trp
145                 150                 155                 160

Ile Arg Asn Phe Thr Asn Cys Pro Leu Trp Val Thr Ser Cys Ser Gly
                165                 170                 175

Thr Met Arg Lys Gly Glu Leu Phe Thr Gly Trp Pro Ile Leu Val
            180                 185                 190

Glu Leu Asp Gly Asp Val Asn Gly His Lys Phe Ser Val Ser Gly Glu
            195                 200                 205

Gly Glu Gly Asp Ala Thr Tyr Gly Lys Leu Thr Leu Lys Phe Ile Cys
210                 215                 220

Thr Thr Gly Lys Leu Pro Val Pro Trp Pro Thr Leu Val Thr Thr Phe
225                 230                 235                 240

Gly Tyr Gly Val Gln Cys Phe Ala Arg Tyr Pro Asp His Met Lys Gln
            245                 250                 255
```

```
His Asp Phe Phe Lys Ser Ala Met Pro Glu Gly Tyr Val Gln Glu Arg
            260                 265                 270

Thr Ile Phe Phe Lys Asp Asp Gly Asn Tyr Lys Thr Arg Ala Glu Val
            275                 280                 285

Lys Phe Glu Gly Asp Thr Leu Val Asn Arg Ile Glu Leu Lys Gly Ile
290                 295                 300

Asp Phe Lys Glu Asp Gly Asn Ile Leu Gly His Lys Leu Glu Tyr Asn
305                 310                 315                 320

Tyr Asn Ser His Asn Val Tyr Ile Met Ala Asp Lys Gln Lys Asn Gly
                325                 330                 335

Ile Lys Val Asn Phe Lys Ile Arg His Asn Ile Glu Asp Gly Ser Val
            340                 345                 350

Gln Leu Ala Asp His Tyr Gln Gln Asn Thr Pro Ile Gly Asp Gly Pro
        355                 360                 365

Val Leu Leu Pro Asp Asn His Tyr Leu Ser Thr Gln Ser Ala Leu Ser
    370                 375                 380

Lys Asp Pro Asn Glu Lys Arg Asp His Met Val Leu Leu Glu Phe Val
385                 390                 395                 400

Thr Ala Ala Gly Ile Thr His Gly Met Asp Glu Leu Tyr Lys
                405                 410
```

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

```
Ala Phe Tyr Arg Trp Tyr Ala Lys
1               5
```

<210> SEQ ID NO 181
<211> LENGTH: 184
<212> TYPE: PRT
<213> ORGANISM: Artificial Sequence
<220> FEATURE:
<223> OTHER INFORMATION: Synthetic

<400> SEQUENCE: 181

```
Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Gln Asp Tyr Thr Gly Pro
            85                  90                  95

Val Tyr His Arg Ala Pro Leu Glu Phe Phe Asp Glu Thr Gln Phe Glu
        100                 105                 110

Glu Thr Thr Lys Arg Ile Gly Arg Val Thr Gly Ser Asp Gly Lys Leu
    115                 120                 125

Tyr His Ile Tyr Val Glu Val Asp Gly Glu Ile Leu Leu Lys Gln Ala
130                 135                 140
```

```
Lys Arg Gly Thr Pro Arg Thr Leu Lys Trp Thr Arg Asn Thr Thr Asn
145                 150                 155                 160

Cys Pro Leu Trp Val Thr Ser Cys Ser Val Asp Lys Leu Ala Ala Ala
                165                 170                 175

Leu Glu His His His His His His
            180

<210> SEQ ID NO 182
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any of the 20 proteinogenic amino
      acids

<400> SEQUENCE: 182

Ala Phe Arg Xaa Trp Tyr Ala
1               5

<210> SEQ ID NO 183
<211> LENGTH: 5
<212> TYPE: PRT
<213> ORGANISM: Artificial Sequence
<220> FEATURE:
<223> OTHER INFORMATION: Synthetic

<400> SEQUENCE: 183

Arg Gly Asp Ile Arg
1               5
```